(12) United States Patent
Valles et al.

(10) Patent No.: US 8,101,172 B2
(45) Date of Patent: Jan. 24, 2012

(54) SOLENOPSIS INVICTA VIRUS

(75) Inventors: Steven Valles, Gainesville, FL (US); Yoshifumi Hashimoto, Ithaca, NY (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 271 days.

(21) Appl. No.: 12/378,683

(22) Filed: Feb. 18, 2009

(65) Prior Publication Data

US 2010/0209395 A1    Aug. 19, 2010

(51) Int. Cl.
*A01N 63/00* (2006.01)
*A61K 47/00* (2006.01)
*A23K 1/00* (2006.01)
*C12N 7/00* (2006.01)

(52) U.S. Cl. .... 424/93.6; 424/439; 424/442; 435/235.1; 514/4.5; 514/44 R

(58) Field of Classification Search ................. 424/93.6, 424/439, 442; 435/235.1; 514/4.5, 44 R
See application file for complete search history.

(56) References Cited

OTHER PUBLICATIONS

Wang et al, Genome Biol. 8:R9.1-R9.16, 2007.*
Wang et al, 2007; EE147335.*
Wang et al, 2007; EE142794.*
Wang et al, 2007; EE136457.*
Wang et al, 2007; EE127842.*
Wang et al, 2007; EE132635.*
Valles et al, 2009; FJ528584.*

* cited by examiner

*Primary Examiner* — Kevin K. Hill
(74) *Attorney, Agent, or Firm* — John Fado; Albert Y. Tsui; Lesley Shaw

(57) ABSTRACT

A Unique *Solenopsis invicta* virus (SINV 3) has been identified and its genome sequenced. Oligonucleotide primers have been developed using the isolated nucleic acid sequences of the SINV 3. The virus is used as a biocontrol agent for control of fire ants.

7 Claims, 12 Drawing Sheets

FIG. 1A

```
   1 ttttaaaata ggaaattaaa gtccagtaag gttactggca tttctatttt aactcaaagc
  61 cttcgattc gggtttgcga gaatcaacgc catgctgaa aagacacaaa ctttcgttca
 121 aatgaaact catgttttag acatgacttc tgattttaaa tcagacttat cacttgaaaa
 181 agtgacttca tcagttgaac aaactgatga cttagttagt cttagttact aaaatcatta ataataatga
 241 cttagatatt aaggatcttt cctttttaag gaacttactt ttaagtactt tgcatattt
 301 aggtattgct aaaatttgtag ctattaatat tactttaagt atcttaagta tttaatgtt
 361 acttataaac tcttgtgcta agtttactcg tattgttaat ttaagtagtc atattttaaa
 421 tattataact acttaggct tatacttcca ggtatcctct atggagattg aagaaataac
 481 ccaacttttt gaaaatgaat tcggaactta tgatgatgat aaaattttat ctcactatat
 541 taaaattgt aacttaccta atcgtaaaga tgtatatgaa tatatatctt taaatgattt
 601 aaaatataaa ataaaacttc cggatatttc ttttatgaa cttaaaaatg atatacttc
 661 aaaatataaa aatttacact tatggatttt ccaaaatttt actgatgaat ttctgctat
 721 gtgtttggt gttcaacctt atcgtatttc aatcttcgt gaaatgttag taatatctcg
 781 tcaaggattt attcctaaag atttatttaa tgaaattcga aaattatgta atatgggtgt
 841 ttctgttata attctcttca ttcaatctaa attatttgat gaaccttta aaaagagaga
 901 ttgtacccaa gctttaaaag atgcttctgt tatctcttct ccatttgata ctcctggaa
 961 tcttattctt aaacaagttt gtgataattc tgctgaagag cgatttactc aaactatatt
1021 ggatttaca tctgaattg ataatttcct tggtattcca aattataat ttgctaaaaa
1081 tcaaaatg gtaaaatacta tttctaaatc tcttgatgct tgtgctaaat ttttgttcac
1141 ttgtcctaaa gataaacaaa ctgaaatttt tcctcttcaa ggattacata cgtcattga
1201 taacgtcgt aatgaaattt taactactt tatgccaaaa tttgctcgtc aggaaccatt
1261 tgttgttctt tttcaaggac ctggtggtat tggtaaaact catcttgttc aacaattggc
1321 tactaaatgt gtaaattctt tttatcaaga tcacgaagat gattatattg aaatttcacc
1381 tgatgataaa tattggcctc ctcttttctg acaacgtgtt gcatttttg atgaagctgg
1441 taatttgaat gattaactg aggatctttt tttcagaaat attaaaagta tttgttcacc
1501 tgcatatttt aattgtgctg ctgctgatat agaacataaa atttcccat gtccatttga
1561 attagtgttt gcaactgtaa atactgattt agatactctt caatctaaa tttcttcaac
1621 atttggtcaa gcatctgttt ttccaatttg gcgtcgttgc attgttgttg agtgttcatg
1681 gaatgaaaaa gaattgggac ctttaatta taaaatcct tcggtcatc gttctgatta
1741 tagtcatatt actatgaatt atatgtcata tgatgataaa acctcaaaaat tggctttaga
1801 aaaagaaatt aatttgata cttgtttga tatgttgt ttaagattta gaaagaaaca
1861 acaagaacat gatactaaaa tttctattc aactaatgaa attcaacgtc aatctaattc
1921 taaacaacat ttttctgtat gtttatatgg tgaacctggt caagtaaaa catataacct
1981 taataatta ataacactt tgcaaatgc aactaatctt aaaattggat cagaggaaaa
2041 accttctatc catattttg atgatatat taaagataa aatgatgaa attgctctaa
2101 atttatggat atttataata ataattacc taatattct gtaatatttt ctgcaactaa
2161 tgtttatcct aaaactcatt tcttttccaac atttttctta actaactta tatatgcttt
2221 tattcaacct tttaaacaag ttggactta tcgcagattg ggatttgatg gttatactga
```

```
2281 tattcctaat tcttctgtta atgctccaat ttttgtacaa aatttttaaat tttatgaacg
2341 taaacaacat atttgttatt ttcttcct tgaattttct aaaatataa tttgtttatat
2401 cttcttcttt ttatacttcc cgttaaaatt tataagaaa attgatttaa ttgaaataaa
2461 ggatgtgaac aaatatgttt atgatagata tataaacttc ttatctcttt ctaaacaaat
2521 tgaaattgtt gaatacctc ctaatttgga aatgtttgaa tttgattta gattaatat
2581 gaataaattt catagagttt cttttaataa tccttttgaa ttggataat atattcattt
2641 taataaaaat tcctatgaaa atcttttgca ttttgattgg aaaatgtatc tttcacctag
2701 agttaaacat cgtcttgctt tatcttatga aaaattcttt ataacaattt ctgaagttaa
2761 caagaaata ataattgaag aattaaaacg atatgtttta ctttttaaac aatttaatat
2821 tgatcctaat atggagataa atcttggaga atatggatca ttttattata ttaacggaaa
2881 aattcattta atgacaatta atattgaaag taatgttct gaaattccg ttttttactga
2941 tggtgattat gtttatatt ctgaacataa aatcccgta attgatttat ttgataacat
3001 taatataat tcaaaatata atttgagttt cgatcaatct atagctctaa attcgtttaa
3061 aactggtgat tcattttatt ctaatgctaa agttaggaag agtttatcca aatttgttct
3121 tcttaattat caaactaaat ttaaattata tttaaaagaa gctaaagata aagtaaagaa
3181 ttttattgaa actccaattg gtcattact ctcaatatata ttaaccattt ttgttatttg
3241 ttatgcatca tttaaaattt attctaaatt ttcaaacttt ttcctcaaag atcaagctat
3301 tgaagatcaa agaaaaggag aaagaaaat taagaaaata actaattatg atttctgatgg
3361 tgttcaacct caacgtaaag gtgaaaagaa aattaagaaa gtaactaatt atgattctga
3421 tggtgttcaa cctcaaagta atgttaaagt tgaagagaa attaaattag aacttgatcc
3481 aactgtcaa aaattacttc ttggaaatga tttcactagt gaacttgaaa tatttagttga
3541 actgaaaa gatgatgaag aattactaca atctaaaata gataataaat ctatggctgg
3601 acttcgtaga gaagtaagac gtagacgtta tgctagatcc aagaagctc aaatcgaaaa
3661 acaggaagtt ctcactttac ctgatgtaaa tggatttgaa ggtggtaaac cttattcca
3721 aattgctgaa cccttcaagc tc gtaaaattt atgtcaaatt tatatgattg ctaataatga
3781 aaattgtatt gcttctaaat ttcttgatca tattgtatgt tatgattat ttgtttttaa
3841 aaagagatta gcttcagttg gtcatattgt agaagcactt aagtgcgctc ctggttataa
3901 tctttatgct ggatgtgatc aatttaatgg taaattata aaaatgaatc ttgttcgaaa
3961 ttatcgtaag agggaacttt ctgtttggga tgtcgattgt ccaaatgatt ttgtagattt
4021 aacttcgttt ttcattccta aagaagagct ttatgatgct gaaaattgta atactgttct
4081 tggtcgtttt ggaatgaaca aacgagaagt atatttatat ggtaactgcg aatttattca
4141 agaatttttt aaagtagata ataagggcgc tcaagaattt ggatatattg attgggctac
4201 agtagatata acttaacta caggtggaga ttgtggttta ccctattata tctgtgaaag
4261 gaagaaattc cataataaaa taatgggatt acatttgct ggtaataatg ttaatcataa
4321 aacaattggt atgtctgctt taatttataa tttgtgatgt gtagtttgga aaggagctga
4381 agtcaatct aaatgtaaat aatataaag gttataatca attattgcac aacctgatat
4441 tccaaggaa aaatataaag gttataatca tgaaattgtg tggaattcac ttcatgaatc
4501 ctcaccaaca acctaaatg aagaattgga acattattta aatattttcc ctaaatttac
```

```
4561 aggaacaata attaagcatt ctggtgataa attttatgga agcgtaaaac attctcatac
4621 tcaatttatt tctaaattta aaacagaatt gacagttact aatggttgga aactttcaac
4681 tgctggtgat tgtcaatttg aatctaatca tattctcct aatactgaag taatgtatag
4741 agttgttgac gttcaattca attcgatatt taaagcattt aaatcacaac cttatattaa
4801 aaattccgt ttaattgcaa atgtatatga attttaacgt aaaagatgga aaacaacgtg taactatttt
4861 aacataatt ccgtttctg attttaacgt atttttaacgt ctatgttaca gaagatgttt aagcattagt
4921 tccgctgcat cttaatgaag atgaggaagt ctatgttaca gaagatgttt ctgatatctt
4981 caaaacagct ataaaacgaa aacagcgtgg tatacttcct gatgtgccat acgaaacagt
5041 tgaaatgaa acagttgaaa ttttaggtat aactcataga aatatgactc ctgaaccagc
5101 tcaaatgtat aaccaactc cattctataa attagcatta aaatttaatt tagatcataa
5161 attacctgtt aattttaata tgaaagattg cccacaagaa caaaagaca tgatggttct
5221 agatcgtttg ggacaaccaa accctagaat tactcaatct ttaaaatggg cacataaaga
5281 ttattcaccc gattacgaat taagaaaata tgttaaggaa caatatatgt gtaatataat
5341 ggaatattat gctggatgta acctttgac tgaagaacaa attttaaaag gttatgtcc
5401 taatcataga ttatatggag cacttggtgg aatggaaatt gattcatcta taggatggac
5461 aatgaaagaa ttatatcgag taactaaaaa gagtgatgtt ataaatttag attcaaacgg
5521 taattattct ttttaaca atgaagctgc tcaatataca caagagcttt taaaaatttc
5581 tatggaacaa gcacataatg gtcaacgtta ttatactgct tttaatgaat taatgaaaat
5641 ggaaaatta aaaccttcaa aaaatttat ccctagaact tttactgctc aagatttaaa
5701 tggagttctt atggaacgtt ggattcttgg tgagttcaca gctcgtgcac ttgcttggga
5761 tgaaaattgt gccgtaggat gtaatccata tgcaacattt cataaatttg ctacaaaatt
5821 ctttaaattt aaaaatttct tttcttgtga ttataaaaat tttgataga caattccaaa
5881 atgtgttttt gaagattta gagatatgct tattcaagct aatcctcata tgaaaaatga
5941 aatttatgct tgtttccaaa caataattga tcgtatacaa gtaagtggaa attcgatatt
6001 acttgtacat ggtgtatgc cttcaggatg tgtaccaact gctccattga attctaaagt
6061 taatgatata atgatttata cagcttatgt taatatatta agacgtgctg atagaggtga
6121 tataacttct tatcgttact atagagattt agtttgtaga ttattttatg gagatgatgt
6181 tattatagca gttgatgatt caattgctga catcttaat tgccaaacac tttctgaaga
6241 aatgaaaatc ttatttggta tgaatatgac tgatggttct aaaagcgata ttattccaaa
6301 atttgaaact attgaaacat tatctttat attcaagatt ttccgaccac ttaaacatca
6361 agaaaattt atagttggtg cttttaaagaa aatttctatt caaactcatt ttttattatgc
6421 aactgatgat actcctgaac attttggtca agtattttaaa acaattcagg aagaagctgc
6481 attatgggaa gaagaatatt tcaataaaat tcaatcgtat attcaagaaa ttataagaaa
6541 atttccagaa attctcaaat tcttttaattt tgaatcttat aaatcaattc aaaaaacgata
6601 tattatgaat ggttgaatg aattgtcaa acttgaaaag cttgacttaa atttaaataa
6661 gaaaaagtcc agtaaggtta ctggcatcca ttcgaaacaa tattcgaagt ttcttaagtt
6721 tttgtcgaga atcgaaacg aaaaagctgc ccttgaaggc aattttaata aagaaagtgt
6781 taatacctgg tatttaaga tgtcaaaggc tatgcacctc aatgaaatct ttcaaaaggg
```

```
6841  cctcatctct  aaacccctig  ctgaatttta  ttttaacgag  ggtcaaaaaa  tgtgggattg
6901  caatattact  ttccgtcgtt  ctaaagacga  tctcccttt   acgttctctg  gctcaggcac
6961  tacaaaagct  tgtgcgcgtg  aacaggccgc  tgaagaagcg  cttgttctct  ttagccaaga
7021  agatgaaata  gttcgtcaaa  taaacgatat  tcaatcagat  tgtaaatttt  gtaagaaaat
7081  gattcgatat  aaaaacttc   tatctggtgt  ttcaattcaa  cgtcaaatga  atgtttcaaa
7141  aattaccgaa  aatcatgttc  cttctgctgg  tatgatggca  acagatcctt  ctgttgctcc
7201  agattctggc  attgcaacta  atacacaaac  tccttcgatt  tccgtgtat   tgaatcccat
7261  agctagagca  ttagataatc  ctgctggaac  tgtgctccc   ttgataaac   atacttatgt
7321  ttataatgtc  tttactcgtt  ggccggaaat  gagtaccgta  ttgaacaaat  cattggctgc
7381  tggagctgaa  gtatttaaaa  tttctcttga  tcctaataaa  ttacctaaaa  gaatttaca
7441  atatattcaa  tttcataaaa  ctataattcc  tcaaatagaa  gttcaaattc  ttattggtgg
7501  tgctgctgga  acagttggtt  ggcttaaagt  cggctgggtt  cctgatgcaa  gtactgctaa
7561  aaagtattca  ttggatgatt  tacaattggt  tgcttcagaa  acaattaatt  tgaattcaac
7621  aataacaatg  tcgatgataa  taaatgatag  ccgtagaaat  ggtatgttta  ggcttactaa
7681  aagtgatcct  gaaccttggc  ctggtatgt   ttgtttagtc  gaacatccta  taactaatgt
7741  tcaaagaaat  gatgatgtta  attatccagt  tattgttagt  gttagacttg  gtcctgattg
7801  ccagctaatg  cagccttaca  atgatttaaa  ctgagtggag  gcacagatcc  agatcctgat
7861  cctgaaccgg  atccggatcc  agagcctggg  cccgaccctg  aaccaggggt  cgatgaactc
7921  gatcttagta  aatatattcc  aaatcaactt  attgatttgc  ttatttgtaa  tagttatgtt
7981  ccaaataatg  taagcgttga  ttttctaagt  acctatccaa  atttaaattt  ttcaattcat
8041  aatataactg  atgttgtggt  ttcttcaaaa  ccatatacac  ttgctctttt  tgaaactgaa
8101  agtcaaatta  atttcgctag  tgtttggaga  ggtgatttaa  ctcaattaag  tgtttttatt
8161  caatataaat  tttatactcg  tgtagaagca  tataataaag  taactacagt  tcatacagat
8221  aaatggactc  caaatttcga  tggtactgtt  tataaacctg  tggatgttaa  aattgaacat
8281  gcatatgaa   cttatgaatt  aacaacaatg  tggctaactt  cttatgatt   ggttatggaa
8341  tggtcactag  atgaaagtag  agtctttat   ggtacttata  aaactgattc  taatggtcgg
8401  agatggttaa  ttgatggtaa  cacaccaatt  gctagatctg  atcattgttt  catcgtttca
8461  tcacctgatc  ttcttagtga  tgataaagct  tactataata  acctattgg   agcaaaacaa
8521  ggtggaaagc  ttgttgatgg  agcacagatt  taccgtatat  ttaaaactga  aagtggagga
8581  tatcgtctg   atccttttgt  cccttgaaaca tattggccat  ctgaaactcc  ttataatgct
8641  gattggtcag  gtgttaaaat  gccttatcaa  attagaaag   taattcaaac  tggaaataat
8701  ttagcaggaa  aacatcttga  tggagatctt  aaaatgtgtg  ctatgataag  gcaaggttcc
8761  tctagcactc  aatctactga  taattattc   taccaattc   atgttcataa  tttctctgca
8821  ttgttaaaac  aaatgaattt  aatttttaaa  gaacgaaaaa  ctaaatatat  taaatttgat
8881  ttacaagtgg  gtgcaaacc   attgctcaa   atgggctttg  gtgatgcgc   cttattgga
8941  agaactacaa  tgtttagaca  aattcgggct  gctataacaa  atgttatttt  acttaaaat
9001  atcgttggcg  tagatgattt  atctggatta  caagcattac  caacttctgg  ttttgctgat
9061  tgggttgtta  aagctcaatc  tacaaattca  aaatttttaa  atgattttta  taatgataaa
```

```
9121  atttcaatag aacgtcaagc gagtcttgga attgctgctg ctattggtgc tggtcaagga
9181  cttttcgggg gactttcagc ccaatggcaa tggcaacaac aagcagattg gtctcgtcaa
9241  atgcagagag aacgacttga tatgatggaa aaattagcaa atataaataa tcaagctcgt
9301  ttaaatcaat taaccaatc tggagctcaa caaagaataa ctcaacaagc tgcttatcaa
9361  caacaaatga atgctcttgg agctggttct gtgtccgctc aaaatggtat gtatactcca
9421  tctaattata caccattacc tagttataag tcaaatacta ctaattatta taataatagt
9481  gtttatcata ctgataataa tattactaat aatccttcta atacatcttt aactaataat
9541  attaataatt ttaatcctga attatttcaa caacaaagag aacgtatgcc tactccatca
9601  gaagcatatg ataattctaa aggtttgta cctcaacctg ggacatcaaa atctattgct
9661  actgaaaata ttaatccaaa ttataaagat gaggaacata tttatgaacc tattgaacaa
9721  caaaatcatg aatatgctga tattgattat acgctatga atatttcgcg tgaaaataaa
9781  aactcttcta attttggaaa tgttggcatt ttggatcatc aatatgctga tattgattat
9841  gatgctatga aaatagctcg tgatcaacaa aattcaagta aatttggtaa tgttggtgtt
9901  ttaaccatc aatatgctga attagatttt tcaaaaaata atacacgtaa aaattcacaa
9961  attttggata attctttata ttctaaaact caaccatctt caaaatgat tgataattct
10021 ttatatggaa taaatccaaa taaatggtt gaaaatcaaa attatgaacc tgcttctatg
10081 gaacgtaaaa attcaattta ttcttcaaat ttaaattctt ctaataattt gaaatttaat
10141 aatattccaa attttaaagg tcctactact accagctatt aataaatata ctgacttttc gaaacctaat
10201 tttggttctg gaataattca accagctatt aataaatata ctgacttttc gaaacctaat
10261 taatcttaga ttttaaatcc acacttaatt ttaagttagt tatttaaatg tttgtttaa
10321 tttttgtttg atcttcgcat ttttgtggag gtgcgaagat taatcataat gtaaagtttt
10381 tcaaacaaaa aaaaaaaaaa a //
```

|        |      | I | II | III | IV |
|--------|------|---|----|-----|----|
| KFV    | 3015 | LKDELKIQKT..YKGRQFSAADPLLIPLERKYLGQFLAKAVK...YDKEVNVGMDPILDPHE-13-VDFVSMDKKIPA |
| SINV-3 | 1848 | MMMEKLKPSEN..FIPRITFTAQDLNGVLMERWILGEFTARALA...WDENCAVGCNPYATPHK-13-QDYKNFDRTIPK |
| SINV-2 | 1815 | RPINKVLGDETTPPKTRSVTCMNVYYIPAWRRYTMREWSAMHRAADGTSMFGPGINPEGPEWS-14-FDVSNMDGPLPA |
| SINV-1 | 1052 | LKDERRPIEKVDALKIRVFSNGPMDFNLAFRKYPLGFIAHLMENR.IDNEVAICTNVYSRDWT-15-QDFSNFDGSLNA |
| HAV    | 1904 | PKDELRPLEKVLESKTRAIDACPLDYSILCRMYWGPAISYFHLNPGFHTGVAICIDPDRQWDE-14-LDFSAFDASLSP |

|        |      | V | VI | VII | VIII |
|--------|------|---|----|-----|------|
| KFV    | 3140 | NGTMASCCVATAPINSVILNNFLM-25-QISYCGDDRWIST.D..LDWFNMVI-26-PLDQISLISRYPR...KLPSGV |
| SINV-3 | 1973 | HGGMPSGCVPLTAPINSKVNDIMI-27-RLFYCGDDVIIAVDDSIADIENCQL-26-TIETLSFISRFFRP.LKHQENP |
| SINV-2 | 1951 | SRGIISGPPGTAEVNTLAHILLI-24-AILYGDDILLTIHDDIIHLFNGKV-25-PLSQCQFHKSSWR...QLLPGY |
| SINV-1 | 1184 | THSQPSGNPATTPIANCLINSIGL-36-LISYCGDDNVIHPLISHLEMNI-27-TLEEVSFLKRGPIFN..BERNC |
| HAV    | 2035 | CGSMPSGSPCTALNSIDNNVNL-22-..CYGDDVLIVFSR.DVQIDNLDL-27-PVSELTFLKRSFN....LVEDR |

SOLENOPSIS INVICTA VIRUS

BACKGROUND OF THE INVENTION

1. Field of the Invention

This invention relates to biological methods and products useful for the control of *Solenopsis invicta*. More specifically, the present invention is directed to a novel *Solenopsis invicta* virus, nucleic acids encoding the novel virus, biocontrol compositions, and methods of using the virus and/or biocontrol compositions for control of fire ants.

2. Description of the Related Art

Red imported fire ant, *Solenopsis invicta* (Buren), was first detected in the United States near Mobile, Ala. in the late 1920s (Loding, USDA Insect Pest Surv. Bull., Volume 9, 241, 1929). Since that time, it has spread to encompass more than 128 million hectares, from Virgina, south to Florida and west to California. (Williams et al., Am. Entomol., Volume 47, 146-159, 2001). Efforts to control, prevent, repair damage, and otherwise to mitigate the effects of this pest ant are estimated to exceed 3 billion dollars annually (Pereira, J. Agric. Urban Entomol., Volume 20, 123-130, 2004). Fire ants are known to destroy young citrus trees, growing crops, and germinating seeds. This has an economic impact on agriculture in infested areas. Telephone companies spend substantial amounts of money each year treating their electrical equipment to prevent fire ant invasion because fire ants accumulate at electrical contacts and can short out electrical equipment. Farm equipment can also be damaged by large fire ant mounds. Fire ants also present a danger to wildlife, such as ground nesting birds and animals. Furthermore, fire ants are known to excavate the soil from under roadways causing damage.

Fire ants also pose health care problems to millions of people stung each year—a significant number of which require medical care. Fire ant stings are also blamed for human deaths. Consequently, there is much interest in controlling these troublesome pests.

This interest has resulted in much research and resources being expended through the years to develop reagents and methods for controlling fire ants. While many useful insecticide formulations have resulted from this research, the problems associated with fire ants still exist because the relief gained by insecticide use is only temporary. Once the insecticide pressure is relaxed, fire ant populations invariably repopulate the areas. This reinfestation ability is attributed to the high reproductive capabilities, the efficient foraging behavior, and the ecological adaptability of the ants. While effective for controlling ants in relatively small defined areas, insecticides can create other problems. For example, some insecticides, which are effective at controlling fire ants, can pose a significant threat to the environment, including birds and mammals.

Although considerable research effort has been brought to bear against the red imported fire ant, it remains the primary pest ant species in infested areas; initial eradication trials failed, yielding to the wide distribution of pesticide-based control products and a federally imposed quarantine to prevent further spread. Recently, much of the research effort has focused on elucidating basic life processes in an attempt to develop unique control measures, and fostering the development of self-sustaining methods of control, including biocontrol organisms and microbes (Williams et al., Am. Entomol., Volume 49, 150-163, 2003).

Despite intensive searches over the last 4 or 5 decades for viral infections of *S. invicta*, only recently were the first viral infections reported and characterized from this ant (Valles et al, Virology, Volume 328, 151-157,2004; Valles and Strong, 2005; Valles et al., Virology, Volume 365, 457-463, 2007; J. Invert. Pathol., Volume 99, 74-81, 2008). *Solenopsis invicta* virus 1 (SINV-1) is a positive-strand, RNA virus with characteristics consistent with viruses in the Dicistroviridae (Mayo, Arch. Virol., Volume 147, 1655-1656, 2002). It possess a monopartite, single-stranded, 3'-polyadenylated, RNA genome that encodes 2 polyproteins. The 5'-proximal polyprotein contains sequences with identity to RNA-dependent RNA polymerase (RdRp), helicase, and cysteine protease proteins characteristic of single-stranded RNA viruses (Koonin, J. Gen. Virol., Volume 72, 2197-2206, 1991) and the 3'-proximal polyprotein contains sequences consistent with viral coat proteins which was confirmed by purification and N-terminal sequencing (Hashimoto and Valles, J. Invertebr. Pathol., Volume 99, 136-140, 2008). *Solenopsis invicta* virus 2 (SINV-2) is also a positive-strand RNA virus but with an unusual genome organization (Valles et al., 2007, supra). The SINV-2 genome is monopartite and polycistronic, with 4 open reading frames in the sense orientation (Valles et al., 2007, supra). SINV-1 and-2 have been associated inconsistently with colony death (Valles et al., 2004; 2007; Hashimoto and Valles, 2008, supra).

Use of positive-strand RNA viruses as insect control agents has been proposed (Scotti et al., Adv. Virus Res. Volume 26, 117-143, 1981; Insect viruses: new strategies for pest control, 128-163. In Oakshott, J. Whitten, M. J. (eds) Molecular approaches to fundamental and applied entomology. Springer Verlag, New York, N.Y. et al, 1993) and successfully demonstrated for the olive fruit fly (Manousis and Moore, Appl. Environ. Microbiol., Volume 53, 142-148, 1987) and *Helicoverpa armigera* (Christian et al., J. Econ. Entomol., Volume 98, 1839-1847, 2005). However, production of pure virus has been limited to in vitro systems (cell culture). A cell line is not available for *S. invicta* which has hampered development and use of the *Solenopsis invicta* viruses as control agents against fire ants. Recently, successful in vitro expression of a positive-strand RNA virus was reported (Pal et al., J. Virol., Volume 81, 9339-9345, 2007; Boyapalle et al. Virology, Volume 375, 401-411, 2008). A clone of the *Rhopalosiphum padi* virus genome was expressed in a baculovirus expression system and found to be infectious and pathogenic to its aphid host (Pal et al., 2007; Boyapalle et al., 2008; both supra).

A dearth of natural enemies of the red imported fire ant have been found in the U.S. including a neogregarine (Pereira et al., J. Invertebr. Pathology, Volume 81, 45-48, 2002) and a fungus (Pereira et al., J. Invertebr. Pathology, Volume 84, 38-44, 2004).

U.S. Pat. No. 6,660,290 discloses a non-sporulating mycelial stage of an insect-specific parasitic fungi for control of pests with fire ants listed as one of many examples of insects controlled by the biopesticide.

U.S. Pat. Nos. 4,925,663; 5,683,689; 6,254,864; and 6,403, 085 disclose a biopesticide effective against fire ants that includes the fungus *Beauveria bassiana*.

There remains a need for biocontrol and/or microbial control agents that eliminate or at least reduce the spread of fire ant colonies using novel pathogens. The present invention described below is directed to a novel *Solenopsis invicta* virus useful for the control of fire ants which are different from prior art pathogens and their uses.

SUMMARY OF THE INVENTION

It is therefore an object of the present invention to provide a novel *Solenopsis invicta* virus (SINV-3) for biocontrol of *Solenopsis invicta*.

Another object of the present invention is to provide a novel *Solenopsis invicta* virus (SINV-3) identifiable by a primer selected from the group consisting of SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 21, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, and SEQ ID NO 33.

A further object of the present invention is to provide a nucleic acid sequence SEQ ID NO 1 for SINV-3.

Another object of the present invention is to provide a biocontrol method for controlling fire ants that includes applying a SINV-3 virus and a carrier that is a fire ant food source to form a biocontrol composition which is scattered near a fire ant colony.

Another object of the present invention is to provide a biocontrol composition comprising SINV-3 and an acceptable carrier.

Further objects and advantages of the present invention will become apparent from the following description.

BRIEF DESCRIPTION OF THE DRAWINGS

FIGS. 1(A-1(E) shows SEQ ID NO 1 of the present invention

FIG. 4 shows the alignment comparisons of predicted amino acid sequences of the

RdRp of KFV, SINV-1, SINV-2, SINV-3 and Hepatitis A virus (HAV). The numbers on the left indicate the starting amino acids of aligned sequences. Identical residues in at least four of the five virus sequences are shown in reverse. Sequences motifs shown for RdRp (I-VIII) correspond to those identified and reviewed by Koonin and Dolja (Crit. Rev. Biochem. Molec. Biol., Volume 28, 375-430, 1993). SEQ ID NO: 44, 45, 46, 47, and 48 correspond to KFV motifs of I-III, IV, V, VI-VII, and VIII respectively. SEQ ID NO: 49, 50, 51, 52, and 53 correspond to SINV-3 motifs of I-III, IV, V, VI-VII, and VIII respectively. SEQ ID NO: 54, 55, 56, 57, and 58 correspond to SINV-2 motifs of I-III, IV, V, VI-VII, and VIII respectively. SEQ ID NO: 59, 60, 61, 62, and 63 correspond to SINV-1 motifs of I-III, IV, V, VI-VII, and VIII respectively. SEQ ID NO: 64, 65, 66, 67, and 68 correspond to HAV motifs of I-III, IV, V, VI-VII, and VIII respectively.

Figure 5:
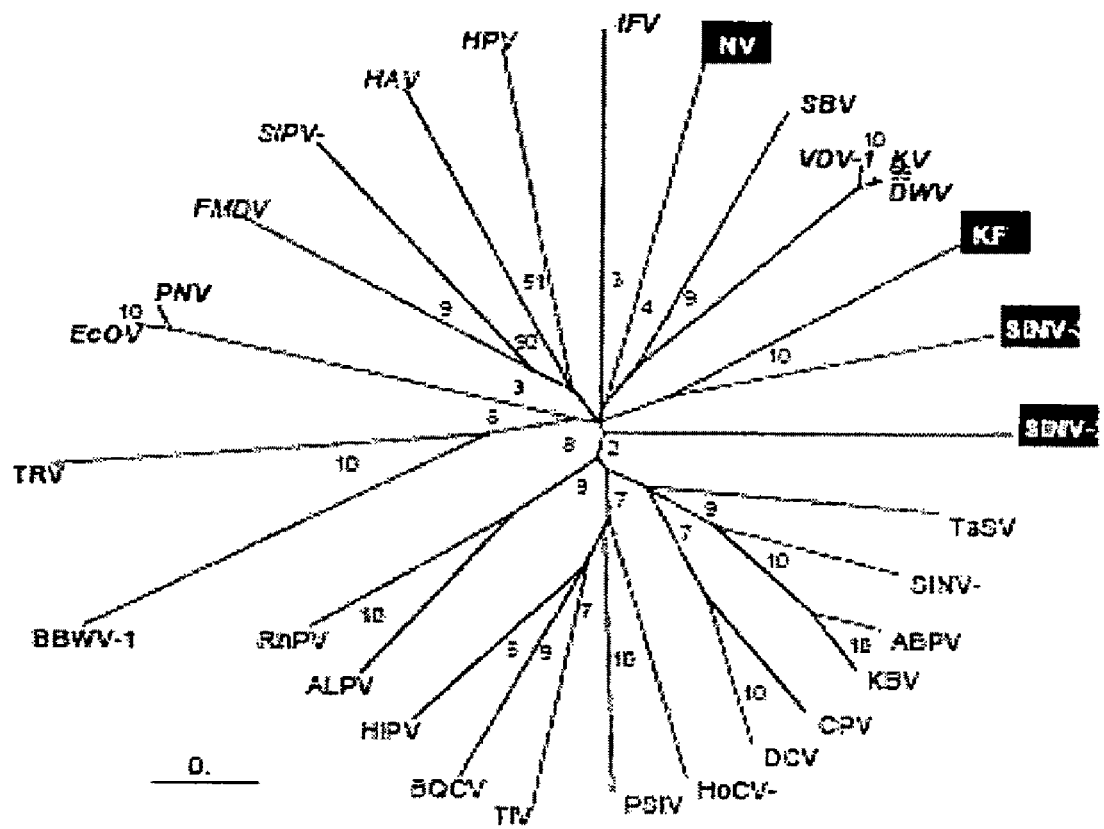

FIG. 5 shows a phylogenetic analysis of the conserved amino acid sequences containing domains I to VIII of the putative RdRp from thirteen dicistroviruses (unaltered text font), seven iflaviruses (bold, italic), two plant RNA viruses (bold), four picornaviruses (italic), and four unassigned viruses (white text). Virus abbreviations, accession number of the virus RNA protein sequence, and amino acid residues of aligned sequences in a specific ORF (5' proximal ORF of dicistroviruses, otherwise an ORF number is specified) include: Aphid lethal paralysis virus (APLV) [AD536531], 1661-1995; Black queen cell virus (BQCV) [NP620564], 1317-1585; Cricket paralysis virus (CPV) [NP647481], 1423-1697; *Drosophila* C virus (DCV) [AF014388], 1415-1693; Himetobi P virus.(HiPV) [AB17037], 1441-1710; *Plautia stali* Intestine virus (PSIV) [NP620555], 1465-1739; *Rhopalosiphum padi* virus (RhPV) [AF022937], 1625-1916; *Triatoma* virus (TiV) [AF178440], 1446-1716; Acute bee paralysis virus (APV) [AAG13118], 1566-1837; *Homalodisca coagulata* virus (HoCV-1) [DQ288865], 1446-1716; Kashmir bee virus (KBV) [AY275710], 1594-1864; *Solenopsis invicta* virus-1 (SINV-1) [AY634314], 1052-1327; Taura syndrome virus (TaSV) [AF277675], 2628-2899; Infectious flacherie virus (IFV) [AB000906], 2618-2888; *Perina nuda* virus (PNV) [AF323747], 2628-2899; Sacbrood virus (SBV) [NC002066], 2522-2790; Deformed wing virus (DWV) [AJ489744], 2556-2826; *Ectropis ibliqua* picorna-like virus (EcOV) [AY365064], 2629-2900; Kakugo virus (KV) [AB070959], 2556-2826; Varroa destructor virus-1 (VDV-1) [AY251269], 2556-2826; Foot and Mouth disease virus (FMDV) [AF308157], 2011-2264; Hepatitis A virus (HAV) [NC001489], 1904-2161; Human parchovirus (HPV) [AJ005695], 1871-2117; Simian picornavirus 1 (SiPV-1) [AY064708], 2119-2368; Broad bean wilt virus 1 (BBWV) [NP951030], 405-657; Tomato ringspot virus (TRV) [ABG23688] RNA1, 406-672; Nora virus (NV) [DQ321720], ORF 2, 1763-2026; *Solenopsis invicta* virus 2 (SINV-2) ORF 4 [ABQ01575], 1814-2081; Kelp fly virus (KFV) [YP415507], 3015-3272; *Solenopsis invicta* virus 3 (SINV-3)

Figure 6:
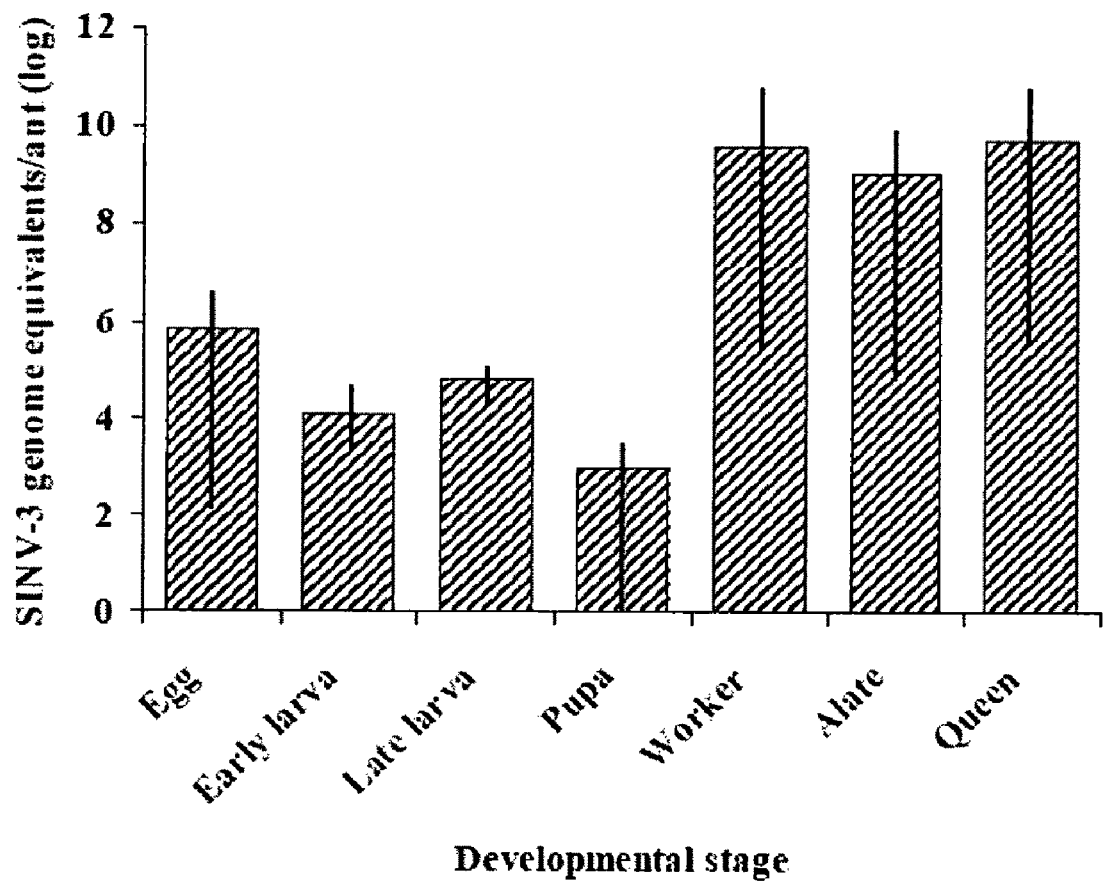

FIG. 6 is a graph showing SINV-3 genome equivalents determined for different developmental stages. Genome equivalents were interpolated from a standard curve generated simultaneously from a plasmid construct. Mean values are indicated by the bar and the internal bar signifies the minimum and maximum value observed for each group.

Figure 7:
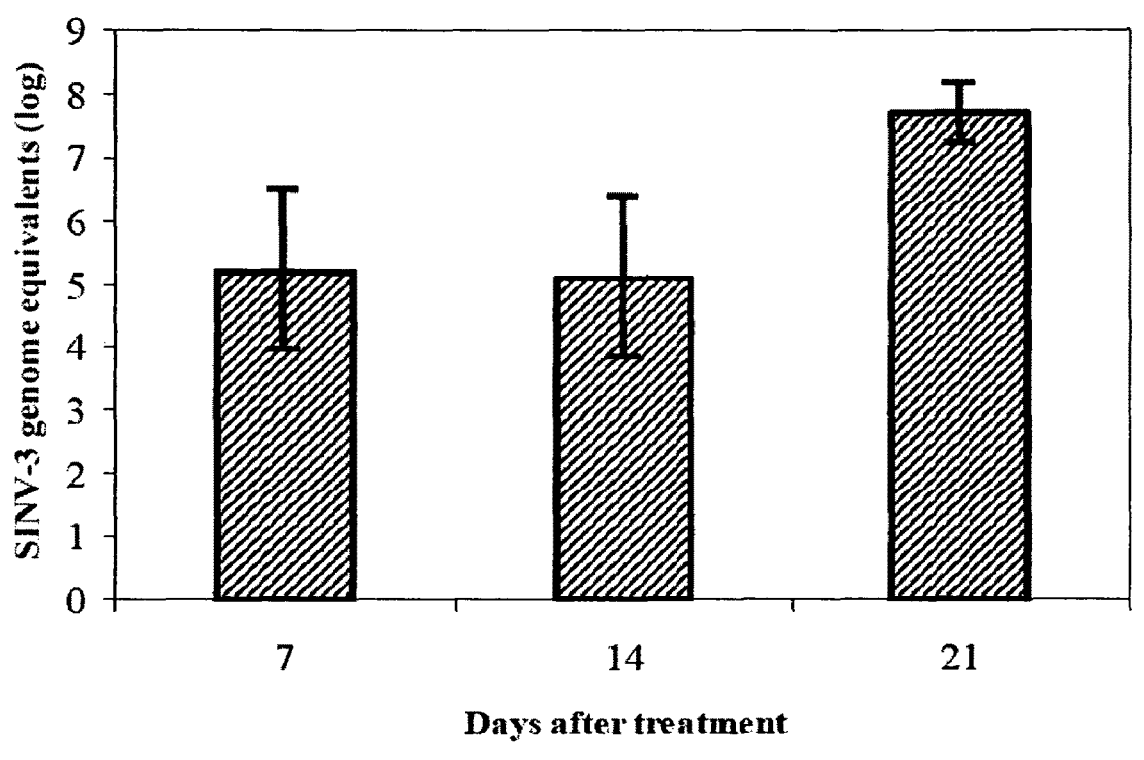

FIG. 7 is a graph showing SINV-3 transmission to uninfected *S. invicta* fragment colonies. Worker ants were sampled on the week specified from each colony and tested for the presence of SINV-3 by QPCR.

Figure 8:
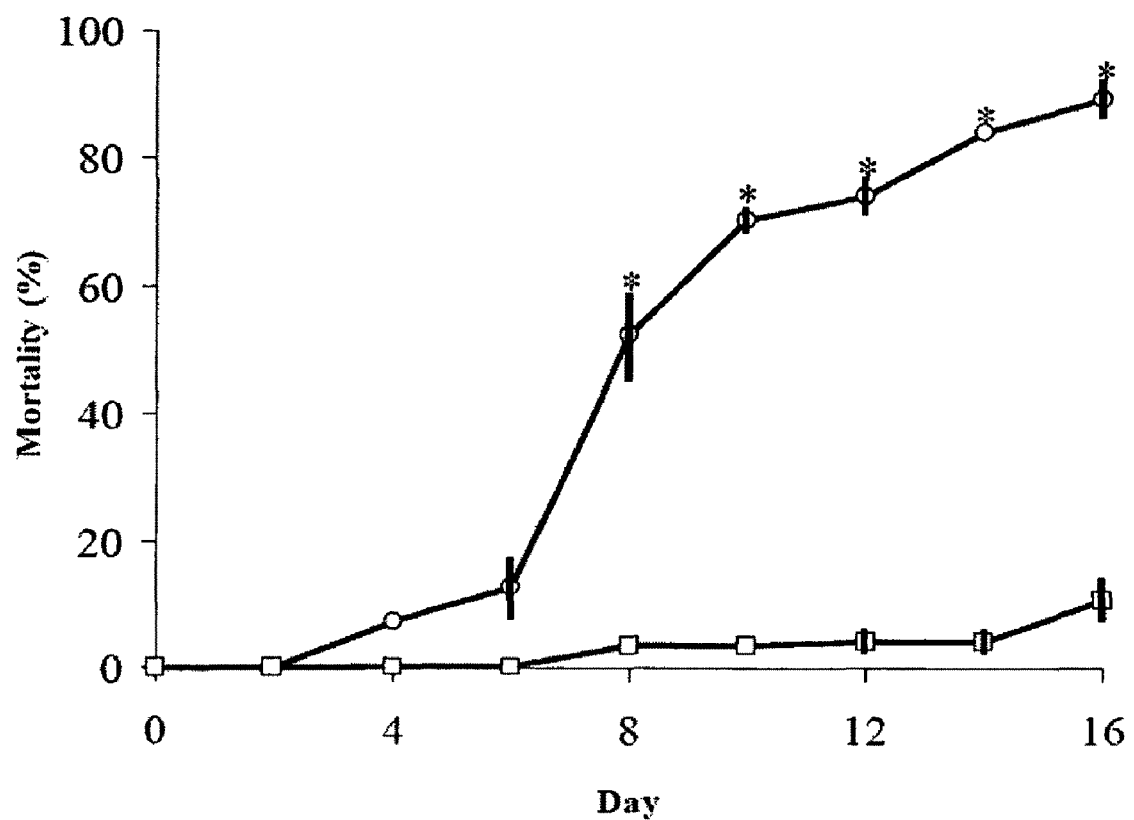

FIG. 8 is a graph showing mortality of *S. invicta* worker ants treated with $10^{10}$ SINV-3 particles (based on QPCR). Open circles are ants treated with SINV-3 and open squares are the control ants (treated with water). Asterisks indicate significant ($p<0.05$) differences for each sample date from the control group by Student's t-test.

DETAILED DESCRIPTION OF THE INVENTION

Although viruses can be important biological control agents against insect populations (Lacey et al., Biol. Comtemp., Volume 21, 230-248, 2001), only recently have they been shown to infect *Solenopsis invicta*. *Solenopsis invicta* viruses (SINV) represent the first infection of the red imported fire ant by this group of organisms. SINV-3, the virus of the present invention, represents the third virus to be discovered from *S. invicta* using the metagenomic approach (Valles et al, 2008, supra) and it possesses features consistent with placement within the order Picomavirales: 1. Non-enveloped particles with a diameter of approximately 30 nm; 2. A positive-sense, single-stranded RNA genome; 3. No production of subgenomic RNA; and 4. A polyprotein containing helicase, protease, and RdRp domains (Le Gall et al., Arch. Virol., Volume 153, 715-727, 2008). Although SINV-1, SINV-2, and the present invention SINV-3 are positive-strand RNA viruses infecting the same host (*S. invicta*), each is distinct phylogenetically (See FIG. 5). Furthermore, they exhibit differences in genome organization; SINV-1 and SINV-3 are discistronic, while SINV-2 is polycistronic. The most important difference between SINV-1, SINV-2 and SINV-3 is apparent pathogenicity. SINV-1 and SINV-2 are similar to many positive-strand RNA viruses that infect honey bees, they are present as chronic, asymptomatic infections that may cause mortality under certain stressful conditions (Bailey, Ann. Appl. Biol., Volume 60, 43-48, 1967; Chen and Siede, Adv. Viral Res., Volume 70, 33-80, 2007). Transmission studies of SINV-1 and SINV-2 to uninfected ants were completed by regular feeding. However, mortality among recipient colonies was an occasional event (Valles et al., 2004; Valles unpublished). The virus of the present invention, SINV-3, showed transmission (FIG. 7) associated with mortality (FIG. 8) and a correspondingly high SINV-3 titer; dead ants typically contained greater than approximately $10^9$ viral particles per ant. Further evidence of SINV-3 virulence is the presence of viral genome copies in all tissues of the ant (Table 3 below, Example 3). In the laboratory, SINV causes brood death of an entire colony and infection of healthy colonies (Valles et al., Virology, Volume 328, 151-157, 2004; Valles et al., J. Invert. Path., Volume 88, 232-237, 2005; both references herein incorporated in their entirety).

Published U.S. patent application Ser. No. 11/780,854, filed Jul. 20, 2007, publication number US2008/0031856, published Feb. 7, 2008 (Valles et al) describes two viruses, SINV-1 and SINV-1A, useful for the control of *S. invicta* (herein incorporated by reference in its entirety).

SINV-3 represents the third virus discovered that infects the red imported fire ant, *S. invicta*. SINV-3 is a unique virus with a genome that differs considerably from other positive-strand RNA viruses.

The present invention provides nucleic acids SEQ ID NO 1 (FIG. 1(*a*)-1(*d*)) which is the whole genome for SINV-3. The invention also provides nucleic acid sequences (SEQ ID NO 2-33; Table 4 in Example 3) capable of selectively hybridizing DNA, RNA, and cDNA sequences which can be derived from SEQ ID NO 1. This primers are useful for identifying any. SINV-3 virus. To isolate SINV-3, RNA from fire ants, collected from a fire ant mound, was extracted from about 20-50 workers using TRIZOL reagent according to the manufacturer's directions (Invitrogen, Carlsbad, Calif.).

With the primers of the present invention and the teachings of the present specification, one of ordinary skill in the art could readily identify SINV-3 viruses of the present invention.

For purposes of the present invention, the term "fire ant" and "*Solenopsis invicta*" are used interchangeably to describe the common red fire ant, originating in South America, but now commonly found in the United States, and Puerto Rico. The term fire ant also is used to describe black fire ants and other hybrid fire ants or other ants that are infected by the viruses of the present invention.

For purposes of the present invention, the term "isolated" is defined as separated from other viruses found in naturally occurring organisms.

For purposes of the present invention, the term "composition" is used to describe a composition which contains the virus of the presently claimed invention, optionally a carrier and optionally a pesticide. The carrier component can be a liquid or a solid material and is an inert, non-repellent carrier for delivering the composition to a desired site. Liquids suitable as carriers include water, and any liquid which will not affect the viability of the viruses of the present invention. Solid carriers can be anything which the fire ant will feed on. Non-limiting examples of solid carriers of the present invention include materials such as corn cob grits, extruded corn pellets, boiled egg yolks, and frozen insects such as crickets.

Optional toxicants include Chlorfenapyr, Imidacloprid, Fipronil, Hydramethylnon, Sulfluramid, Hexaflumuron, Pyriproxyfen, methoprene, lufenuron, dimilin Chlorpyrifos, and their active derivatives, Neem, azadiractin, boric acid based, etc. The toxicant acts as a stressor which may be required to initiate viral replication which in turn results in brood death in the fire ant colony.

The term "effective amount" or "amount effective for" as used herein means that minimum amount of a virus composition needed to at least reduce, or substantially eradicate fire ants in a fire ant colony when compared to the same colony or other colony which is untreated. The precise amount needed will vary in accordance with the particular virus composition used; the colony to be treated; the environment in which the colony is located. The exact amount of virus composition needed can easily be determined by one having ordinary skill in the art given the teachings of the present specification. The examples herein show typical concentrations which will be needed to at least reduce the number of fire ants in a colony.

In the method of using the viruses of the present invention, to reduce or eradicate a population of fire ants, the compositions are delivered to the fire ants by spreading the composition at or near the fire ant colonies. The amount of composition used is an effective amount for producing the intended result, whether to reduce or eradicate the population of fire ants. The composition is prepared by homogenizing approximately 300 workers from a SINV infected colony in an equal volume of water and placing the resulting homogenate on a carrier.

Figure 2:
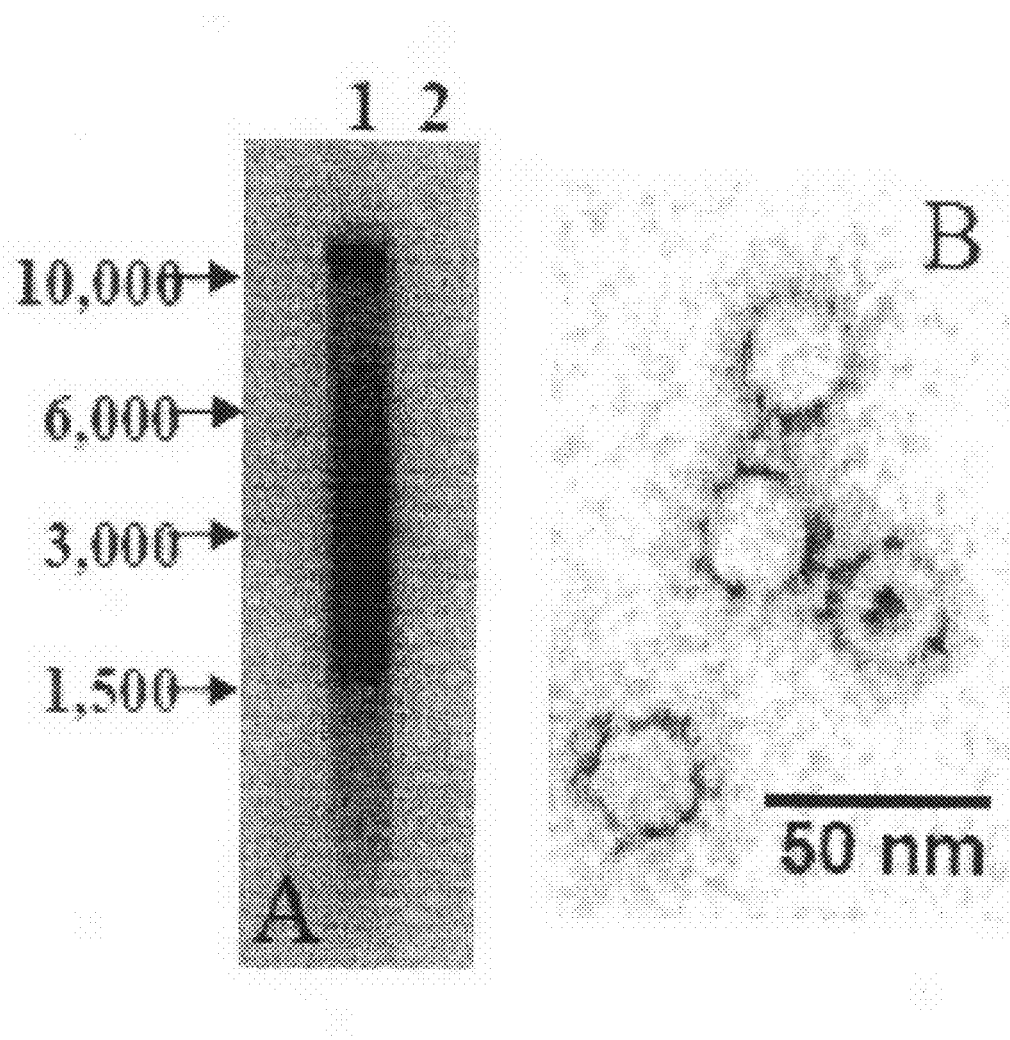
FIGS. 2(A) Is a Northern blot of RNA prepared from purified SINV-3 particles (lane 1) and SINV-3-infected fire ant workers (lane 2). Numbers to the left of the blot indicate the size in nucleotides of single-stranded RNA standards.
FIG. 2(B) is an electron micrograph of a negative stain of purified SINV-3 used for the Northern analysis.

Initial blast analysis (Altschul et al., Nucleic Acids Research, Volume 25, 3389-3402, 1997) of expressed sequence tags (ESTs) from a *Solenopsis invicta* expression library had indicated weak identity of EST 16A4 (Genbank accession number: EH413252) with the polyprotein of *Acyrthosiphum pisum* virus (Valles et al., 2004, supra). Subsequent re-analysis of this EST sequence revealed significant identity with a portion of the kelp fly virus genome (Hartley et al., J. Virol., Volume 79, 13385-13398, 2005). EST 16A4 was therefore used as the primary sequence from which oligonucleotide primers were designed and RACE (3' and 5') reactions conducted to acquire additional sequence and to confirm that this sequence was of viral origin. Subsequent sequence acquisition and analysis confirmed the presence of a new virus from *S. invicta* ants which is SINV-3 (*Solenopsis invicta* virus-3). The 10,386 nucleotide genome is monopartite, biscistronic (non-overlapping), and single-stranded. The genome size was confirmed by Northern analysis in which a band was observed at approximately 10,968±270 nucleotides; no subgenomic RNA was evident. Blastp analysis of ORF 1 resulted in recognition of a conserved domain for RNA-independent RNA polymerase (RdRp) characteristic of positive-strand RNA viruses (Koonin and Dloja, 1993, supra). These viruses invariably possess 8 common sequence motifs in the RdRp (Koonin, J. Gen. Virol., Volume 72, 2197-2206, 1991); all eight of these motifs were present in SINV-3 (See FIGS. 2 and 3). Further, sequence motifs IV, V, and VI were reported to be unequivocally conserved throughout this class of viruses exhibiting 6 invariant amino acid residues (Koonin and Dolja, 1993, supra). These core RdRp motifs were shown by site-directed mutagenesis to be crucial to the activity of the enzyme (Sankar and Porter, J. Biol. Chem., Volume 267, 10168-10176, 1992). SINV-3 possessed all 6 of these characteristic residues $D^{1920}$, $D^{1925}$ (motif IV), $G^{1979}$, $T^{1983}$ (motif V), and $D^{2028}$, $D^{2029}$ (motif VI).

Alignment of SINV-3 ORF 1 with nonstructural polyproteins of positive-strand RNA viruses revealed domains for helicase and protease. Three sequence motifs are conserved among positive-strand helicases, designated A, B, and C (Gorbalenya et al., FEBS Lett., Volume 262, 145-148, 1990). The consensus sequence for motif A, $GX_4GK$ (Gorbalenya et al., 1990, supra), thought to be responsible for nucleotide binding, was found in the translated ORF 1 of SINV-3 at amino acid position 396 ($G^{396}$). Motifs B and C were also identified based on the presence of conserved residues ($Q^{441}$, $D^{447}$-motif B; and $N^{497}$ preceded by a stretch of hydrophobic residues) (Goralenya et al., 1990, supra).

Characteristic motifs for a 3C-like protease, but not a 2A protease, were also detected in the translated ORF 1 of SINV-3. Amino acids thought to form the catalytic triad of the 3C-like protease, $H^{1258}$, $D^{1309}$, and $C^{1381}$ were present in SINV-3 ORF 1 (Koonin and Dolja, 1993, supra; Ryan and Flint, J. Gen. Virol., Volume 78, 699-723, 1997; Luke et al., J. Gen. Virol., Volume 89, 1036-1042, 2008). Furthermore, the consensus GxCG sequence motif was present at amino acids 1379 to 1382.

Phylogenetic analysis of SINV-3 RdRp showed a close relationship with KFV (FIG. 5). Many of the unique features exhibited by KFV are also shared by SINV-3, including a smaller virion size (approximately 27.3±1.3 nm, FIG. 2B) with apparent surface projections (Scotti et al., J. Gen. Virol., Volume 30, 1-9, 1976; Hartley et al., 2005) and higher buoyant density (1.39±0.02 g.ml). Another similarity is the presence of only 2 major capsid proteins (VP1 and VP2) as opposed to four which is typical of *Dicistroviridae* or iflaviruses. Despite a close phylogenetic relationship between KFV and SINV-3, their genome structures were different. KFV genome is monocistronic and SINV-3 is dicistronic. They also exhibited poor identity (<10%) among their structural proteins.

SINV-3 was found to infect all stages of *S. invicta*, including the eggs (See FIG. 6). QPCR of different stages shows that immature ants contained significantly lower quantities of SINV-3 compared with adults (workers, alates, and queens).

The following examples are intended only to further illustrate the invention and are not intended to limit the scope of the invention as defined by the claims.

EXAMPLE 1

A one-step reverse transcriptase polymerase chain reaction (RT-PCR) was used t6 identify SINV-3-infected *S. invicta* ants. A 20 ml scintillation vial was plunged into a fire ant mound in the field for several minutes to collect a sample of the worker caste. The ants were returned to the laboratory and RNA was extracted from about 10-20 ants using TRIZOL reagent according to the manufacturer's directions (Invitrogen, Carlsbad, Calif.). cDNA was synthesized and subsequently amplified using the One-Step RT-PCR kit (Invitrogen) with oligonucleotide primers p705-SEQ ID NO 2 and p707 ID NO 4 (Table 4). Samples were considered positive for the virus when a visible amplicon (about 72 nucleotides) was present after separation on about a 1.2% agarose gel stained with ethidium bromide. RT-PCR was conducted in a PTC 100 thermal cycler (MJ Research, Waltham, Mass.) under the following optimized temperature regime:

1 cycle at about 45° C. for about 30 minutes;
1 cycle at about 94° C. for about 2 minutes;
35 cycles at about 94° C. for about 15 seconds;
1 cycle at about 63° C. for about 15 seconds;
1 cycle at about 68° C. for about 15 seconds; and
a final elongation step of about 68° C. for about 5 minutes.

SINV-3 was purified by discontinuous and isopycnic centrifugation. Briefly, approximately 50 grams of a mixture of worker and brood ants were homogenized in about 150 ml of NT buffer (10 mM Tris-HCl, pH about 7.4, approximately 100 mM NaCl) in a Waring blender on high speed for approximately 2 minutes. The mixture was filtered through about 8 layers of cheese cloth and then extracted with an equal volume of chloroform for approximately 10 minutes with constant shaking. The mixture of centrifuged for about 5 minutes at approximately 5,000×g and the supernatant collected by pipette. The supernatant was layered onto a discontinuous CsCl gradient (about 1.2 and about 1.5 g/ml) which was centrifuged at about 190,000×g for about 2 hours in a Ti50.1 rotor. A whitish band visible near the interface was removed and brought to a density of approximately 1.3 grams/ml CsCl. This sample was then centrifuged at approximately 330,000×g for about 16 hours in a Ti70.1 rotor. A whitish band at about 1.39±0.02 grams/ml was collected. The sample was negatively stained with about 2% phosphotungstic acid, about pH 7, and examined with a Hitachi H-600 transmission electron microscope (Hitachi, Pleasanton, Calif.) at an accelerating voltage of approximately 75 kV. Uninfected worker ants were prepared and examined in the same manner and served as controls.

Particles purified from SINV-3—infected fire ants exhibited similar characteristics and migrated to a density of approximately 1.39±0.02 grams/ml CsCl. No corresponding particles were observed in samples prepared from uninfected fire ants. Electron microscopic examination of negatively stained samples from SINV-3-infected fire ants revealed isometric particles with apparent projections and a diameter of approximately 27.3±1.3 nm (FIG. 2B).

EXAMPLE 2

A series of nine 5' RACE reactions were conducted to obtain the upstream sequence of SINV-3 genome using the 5' RACE system (Invitrogen, Carlsbad, Calif.) and primer walking. cDNA was synthesized for about 50 minutes at about 48 degrees C. with approximately 2.5 µg of total RNA extracted with Trizol from purified SINV-3 particles (as described above in Example 1) with a gene-specific oligonucleotide primer (GSP, Table 1), the RNA template was degraded with RNase H, and the cDNA was purified. The 3' end of the cDNA was polycytidylated with terminal deoxynucleotidyl transferase and dCTP. The tailed cDNA was then amplified with a nested, GSP (3' end) and an abridged anchor primer (AAP). Gel purified amplicons were ligated into pCR4-TOPO vector, transformed into TOP10 competent cells (Invitrogen, Carlsbad, Calif.) and sequenced by the Interdisciplinary Center for Biotechnology Research (University of Florida). (See Tables 1 and 2)

Two 3'RACE reactions were conducted with the GeneRacer kit (Invitrogen). cDNA was synthesized from total RNA (approximately 1 µg) using the GeneRacer Oligo dT primer. Amplicons were cloned and sequenced as described for 5' RACE. Two 3' RACE reactions were required because a region of high adenine density (nucleotides 8847-8874) was binding the oligo dT primer upstream of the 3' poly A tail (Table 1).

Northern analysis was conducted to determine the genome size and possibly whether subgenomic RNA was produced following the glyoxal denaturation procedure of Sambrook and Russel (Molecular Cloning, Cold Spring Harbor Laboratory Press, Cold Spring Harbor, N.Y., 2001; herein incorporated by reference in its entirety). Total RNA (approximately 2 to 8 µg) prepared with Trizol from purified SINV-3 particles was denatured with glyoxal and separated on a 1% agarose gel. Electroporesis was conducted at about 60 volts for about 1.5 hours in BPTE buffer (approximately 30 mM Bis-Tris; 10 mM PIPES; 1 mM EDTA; pH 6.5). Gel separated nucleic acids were transferred onto a Nytran Supercharged Nylon membrane by downward blotting in approximately 0.01 M NaOH and approximately 3 M NaCl. After neutralization and blocking in approximately 6×SSC (approximately 0.9 M NaCl, approximately 0.09 M sodium citrate) the blot was pre-hybridized in approximately 0.5 M sodium phosphate (pH approximately 7.2), approximately 7% SDS, approximately 1 mM EDTA for about 2 hours. The 499 nucleotide probe was synthesized by PCR using olignucleotide primers p762 SEQ ID NO 22 and p764 SEQ ID NO 24 (Table 4), $^{32}$P-labeled dCTP, and a clone from the 3' end of the genome as template. The probe was added to the hybridization chamber and incubated for about 16 hours under high stringency conditions at approximately 68 degrees C. After hybridization, the blot was dried and exposed to x-ray film for about 12 hours. Molecular weight of the SINV-3 genome was interpolated with two sets of RNA standards electrophoresed concurrently.

Blastp analysis was conducted with conserved regions of SINV-3 RdRp and helicase of ORF 1. Representative viruses exhibiting significant e-scores ($<10^{-5}$) were included in the phylogenetic analysis and multiple-alignment with SINV-3 using Vector NTI Advance software (Version 10.1.1, Invitrogen). Multiple alignments were carried out for the deduced amino acid sequences of the non-structural and structural polyproteins of viral genomes. Specifically, conserved regions of the RdRp (domains-I to VIII) and helicase (domains A, B, and C) were aligned and subsequently used to construct an unrooted radial phylogenetic tree using the neighbor-joining method(Saitou and Nei, Mol. Biol. Evol., Volume 4, 406-425, 1987) in ClustalX (Thompson et al., Nucleic Acids Res., Volume 22, 4673-4680, 1994). The statistical significance of branch order was estimated by performing 1000 replications of bootstrap re-sampling of the original aligned amino acid sequences. Trees were generated with TreeView (Page, Computer Applications in the Biosciences, Volume 12, 357-358, 1996).

The genome of *Solenopsis invicta* virus 3 was constructed by compiling sequences from a series of nine successive 5'RACE reactions, two 3' RACE reactions, and the sequence of EST 16A4 (Accession number:EH413252; Tables 1 and 2). The SINV-3 genome was found to be approximately 10,386 nucleotides in length, excluding the poly(A) tail present on the 3' end. This genome size was consistent with Northern analysis results of total RNA extracted from purified SINV-3 (FIG. 2A). Northern blotting yielded a band at approximately 10,968±270 nucleotides. No hybridization was observed in RNA extracted from fire ants determined to be free of SINV-3 by RT-PCR as described above in Example 1.

Figure 3:
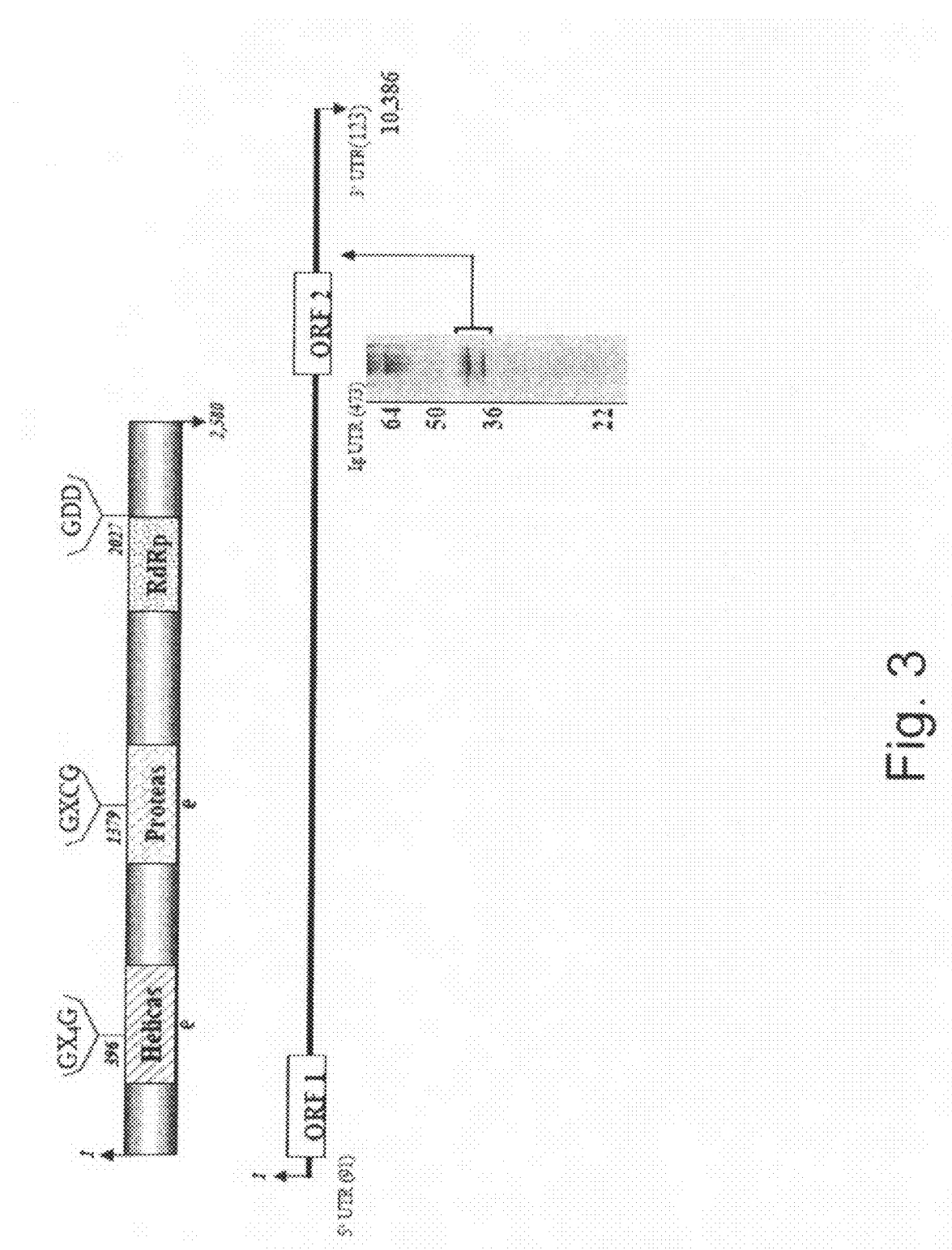
FIG. 3 shows a genome organization of SINV-3. Positions of sequence motifs for helicase, protease, and RNA-dependent RNA-polymerase and their corresponding positions within the polyprotein of ORF 1 are indicated. The italicized numeral indicates the position of the first residue of the sequence provided. The lower right shows results of a silver-stained SDS-PAGE of purified SINV-3 particles. Two bands were consistently observed with a combined molecular mass of approximately 77,250 Da. The predicted molecular weight of the translated ORF 2 was approximately 73,186 Da.

The SINV-3 genome sequence was A/U rich (approximately 70.9% A/U; approximately 29.1% G/C). Analysis of the genome revealed 2 large open reading frames (ORFs) in the sense orientation (out of frame with each other) with an untranslated region (UTR) at each end and between the two ORFs (FIG. 3). The 5' proximal ORF (ORF) commenced at the first canonical (AUG) start codon present at nucleotide position 92 and ended at a UGA stop codon at nucleotide 7,832 which encoded a predicted protein of approximately 299,095 Da (2,580 amino acids). The 3' proximal ORF (ORF 2), commenced at nucleotide position 8,308 (canonical AUG start codon), terminated at nucleotide position 10,261 (UAA stop codon) and encoded a predicted protein at 73,186 Da (651 amino acids). No large ORFs were found in the inverse orientation suggesting that the SINV-3 genome was a positive-strand RNA virus. The 5',3' and intergenic UTRs were comprised of approximately 91, 123, and 473 nucleotides, respectively. Blastp analysis (Altschul et al., 1997, supra) of the translated ORF 1 recognized a conserved domain (GenBank cd01699) for RNA-dependent RNA polymerase (RdRp, FIGS. 2 and 3) which is encoded in the genomes of all RNA viruses with no DNA stage (Koonin and Dolja, 1993, supra). The most significant expectation scores from blastp analysis of the RdRp region of ORF 1 were to Kelp Fly virus (KFV, $10^{-58}$) with corresponding identities of approximately 35.1 and 25.2%, respectively. Helicase and protease sequence motifs were also present in ORF 1 upstream of the RdRp (FIG. 4). Blastp analysis of ORF 2 did not yield any sequences with significant identity. Silver stained SDS-PAGE of purified SINV-3 particles yielded 2 bands (band 1L 41,000 Da; Band 2: 36,250 Da) with a combined molecular mass of approximately 77,250 Da which was similar in mass predicted by ORF 2 (approximately 73,186 Da; FIG. 3).

Phylogenetic analysis of the conserved amino acid sequences containing domains I to VIII of the RdRp (FIGS. 4 and 5) from dicistroviruses, iflaviruses, plant RNA viruses, picomaviruses, and 4 unassigned positive-strand RNA viruses revealed a trichotomous phenogram with SINV-3 and Kelp Fly virus comprising a unique cluster (FIG. 5). The close relationship between SINV-3 and KFV is supported by a significant expectation score and sequence identity when the SINV-3 ORF 1 and KFV ORF were compared by blastp analysis.

TABLE 1

Strategy used to acquire the genome of SINV-3. Successive 5' and 3' RACE reactions conducted,, the corresponding portion of the genome acquired, and oligonucleotide primers used for cDNA synthesis and PCR amplification are indicated.

| | Regions acquired | | Oligonucleotide primers for: | |
|---|---|---|---|---|
| Reaction | (nts, 5'→3') | Size (nts) | cDNA synthesis | PCR amplification |
| 5' RACE | 1-1167 | 1168 | p763 SEQ ID NO 23 | p767 SEQ ID NO: 25/AAP |
| 5' RACE | 1038-1582 | 545 | p722 SEQ ID NO 9 | p762 SEQ ID NO: 22/AAP |
| 5' RACE | 1338-2697 | 1360 | p734 SEQ ID 12 | p755 SEQ ID NO: 20/APP |
| 5' RACE | 2423-3789 | 1367 | p735 SEQ ID NO 13 | p754 SEQ ID NO: 19/AAP |

TABLE 1-continued

Strategy used to acquire the genome of SINV-3. Successive 5' and 3' RACE reactions conducted,, the corresponding portion of the genome acquired, and oligonucleotide primers used for cDNA synthesis and PCR amplification are indicated.

| | Regions acquired | | Oligonucleotide primers for: | |
|---|---|---|---|---|
| Reaction | (nts, 5'→3') | Size (nts) | cDNA synthesis | PCR amplification |
| 5' RACE | 3610-4773 | 1164 | p707 SEQ ID NO 4 | p750 SEQ ID NO: 17/AAP |
| 5' RACE | 4585-5784 | 1200 | p710 SEQ ID NO 6 | p739 SEQ ID NO: 15/AAP |
| 5' RACE | 5636-6333 | 698 | p734 SEQ ID NO 12 | p731 SEQ ID NO: 11/AAP |
| 5' RACE | 6292-6773 | 482 | p722 SEQ ID NO 9 | p720 SEQ ID NO: 8/AAP |
| 5' RACE | 6677-7194 | 518 | p707 SEQ ID NO 4 | p706 SEQ ID NO: 3/AAP |
| 3'RACE | 7164-8869 | 1706 | oligo dT | p705 SEQ ID NO: 2/3' PRIMER |
| EST 16A4 | 7118-7812 | 695 | N/A | N/A |

TABLE 2

Genome sequencing strategy for SINV-3. Oligonucleotide primers used to amplify overlapping regions of the SINV-3 genome. The clone designation and corresponding region of the genome sequence are indicated.

| Clone Designation | Oligonucleotide primers (orientation) | Genome Region amplified |
|---|---|---|
| 12B/178/2 | P791 (F)/p767 (R) | 1-1167 |
| 12B/157/6 | P764 (F)/p756 (R) | 1039-2624 |
| 12B/157/5 | P769 (F)/p752 (R) | 2003-3696 |
| 12B/157/4 | P770 (F)/p748 (R) | 2938-4683 |
| 12B/157/3 | P771 (F)/p738 (R) | 4042-5746 |
| 12B/157/2 | P772 (F)/p734 (R) | 5038-6442 |
| 12B/157/8 | P730 (F)/p708 (R) | 6296-7271 |
| 12B/174/1 | P705 (F)/p713 (R) | 7164-8605 |
| 12B/180 | P775 (F)/p787 (R) | 8038-9730 |

EXAMPLE 3

Tissue tropism of SINV-3 was examined by dissecting different tissues or groups of tissues and quantifying the number of SINV-3 genome equivalents in each respective preparation by quantitative PCR (QPCR). This experiment was conducted for mated queens, workers, and $4^{th}$ instar larvae. Ice-chilled fire ant workers and queens from SINV-3-positive colonies were placed on a glass microscope slide, and head, thorax, and abdomen were separated with a surgical blade under a Leica MS5 dissecting microscope. The head and thorax were placed directly in Trizol and the abdomen was immersed in 1 mM Tris-HCL, pH approximately 8.0, for further dissection. Tissues were isolated and removed from the abdomen with micro-dissecting forceps in the following order: crop, poison sac, midgut, hindgut, Malpighian tubules, fat body (queens only), ovaries (queens only), and the remaining abdominal carcass. Fourth instar larvae from SINV-3 positive colonies were dissected to the following groups: Malpighian tubules, midgut, and remaining carcass. Six replicates were conducted for each stage using individual queens per replicate and pooled groups of workers and larvae (n=10). RNA was extracted with Trizol. cDNA was synthesized from the SINV-3 genome region corresponding to the RdRp with total RNA using SuperScript III Reverse Transcriptase (SsRT; Invitrogen) and a gene-specific primer p707 SEQ ID NO 4 (Table 4). In an approximately 0.5 ml PCR tube, approximately 2 μl of primer p707 SEQ ID NO 4(approximately 1 μM), approximately 1 μl of a dNTP mix (approximately 10 mM), and approximately 10 μl of total RNA (approximately 50 ng) were mixed and heated to about 65 degrees C. for about 5 minutes in a PTC 100 thermal cycler, followed by incubation on ice for about 1 minute. Then, approximately 4 μl of first-strand buffer (approximately 250 mM Tris-HCl, pH about 8.3, approximately 375 mM KCl, approximately 15 mM $MgCl_2$), approximately 2.75 μl of DEPC-treated water, and approximately 0.25 μl SsRT (approximately 200 U/μl) were added. The mixture was incubated at about 55 degrees C. for about 30 minutes, followed by inactivation of SsRT by heating to about 70 degrees C. for about 15 minutes. This cDNA was used to perform QPCR.

QPCR was conducted on an ABI PRISM 7000 Sequence Detection System interfaced to the ABI prism 7000 SDS software (Applied Biosystems, Foster City, Calif.) in an approximately 25 μl reaction volume. The reaction contained approximately 12.5 μl of SYBR Green SuperMix (with UDG and ROX, Invitrogen), approximately 0.4 μl each of approximately 10 μM SINV-3-specific primers p705 and p707, approximately 3 mM $MgCl_2$, approximately 1 μl of the cDNA synthesis reaction, and approximately 10.7 μl of DEPC-water. QPCR conditions consisted of one cycle at approximately 50 degrees C. for about 2 minutes, and approximately 95 degrees C. for about 10 minutes, followed by about 40 cycles at approximately 95 degrees C. for about 15 sec, approximately 64 degrees C. for about 15 sec, approximately 72 degrees C. for about 1 minute. The non-template control for QPCR included a complete cDNA synthesis reaction devoid of RNA template. A standard curve was constructed from a plasmid clone of the corresponding SIN-3 genome region using a copy number range of approximately 5-5×$10^7$ copies. Reaction efficiencies were determined by regressing $C_T$ vales against the template copy number (log) and calculated according to the formula [$E=(10^{-1/slope})-1$] (Klein et al., 1999). Reaction efficiencies reoutinely exceeded approximately 95%.

Experiments were conducted to quantify the SINV-3 infection in different developmental stages of S. invicta. Samples of eggs (n=20), queens (n=11), workers (n=18), early ($1^{st}$-$2^{nd}$ instars), larvae (n=5) and late $93^{rd}$-$4^{th}$ instars) larvae 9n=5) were taken from SINV-3-positive colonies. RNA was extracted from the specimens with Trizol reagent. The RNA concentration was determined spectrophotometrically. The number of SINV-3 genome equivalents in different developmental stages and tissues was quantified by QPCR as described above.

SINV-3 genome was detected in all tissues of S. invicta queens, workers and larvae examined by QPCR (Table 3). The tissues comprising the largest perceintage of SINV-3 genome equivalents was the carcass for queens (approximately 27%) and workers (approximately 50.4%) and midgut (approximately 34.6%) for the larvae. Based on these data, SINV-3 infection appears to be systemic. SINV-3 was detected in S. invicta eggs, workers, larvae, and alate stages (FIG. 6).

TABLE 3

Distribution of SINV-3 genome equivalents among different tissues and tagma of worker, larval ($4^{th}$ instars), queen S. invicta ants.

| Tissue/tagma | Percent of total SINV-3 genome equivalents for stage* | | |
|---|---|---|---|
| | Queen | Worker | Larvae |
| Remaining Carcass[1] | 27.0 ± 3.7 | 50.4 ± 6.7 | 34.4 ± 6.8 |
| Midgut | 9.0 ± 7.5 | 33.6 ± 3.1 | 34.6 ± 6.7 |
| Malpighean tubules | 8.0 ± 5.5 | 3.0 ± 1.2 | 31.0 ± 9.9 |
| Hindgut | 4.2 ± 1.9 | 2.7 ± 0.7 | |
| Poison Sac | 8.2 ± 4.1 | 2.0 ± 1.0 | |
| Head | 13.1 ± 11.1 | 4.5 ± 1.1 | |
| Thorax | 4.0 ± 1.6 | 2.0 ± 0.4 | |
| Crop | 7.3 ± 3.6 | 1.5 ± 0.3 | |
| Ovary | 12.6 ± 7.7 | | |
| Fat Body | 6.9 ± 5.3 | | |

*Mean (±SE) number of SINV-3 genome equivalents was approximately $1.46 ± 2.83 \times 10^6$ for workers, $1.39 ± 3.22 \times 10^9$ for larvae, and $2.0 ± 2.67 \times 10^9$ for queens.
[1] For queens and workers the remaining carcass is comprised of remaining tissues in the abdomen, for larvae the carcass is comprised of remaining tissues of the entire body carcass.

TABLE 4

Oligonucleotide primers used throughout the studies.

| Oligonucleotide Designation | Oligonucleotide (5'-3') | Genome Position | Orientation | SEQ ID NO |
|---|---|---|---|---|
| p705 | CTGCTGGTATGATGGCAACAGATCCTTCTGT | 7164-7194 | → | 2 |
| p706 | ACAGAAGGATCTGTTGCCATCATCATACCAGCAG | 71647194 | ← | 3 |
| P707 | AAGGAGTTTGTGTATTAGTTGCAATGCCAGAATCT | 7201-7235 | ← | 4 |
| p708 | ATGCTCTAGCTATGGGATTCAATACACGGGA | 7241-7271 | ← | 5 |
| p710 | CATCATTTCTTGAACATTAGTTATAGGATGTTCGAC | 7718-7753 | ← | 6 |
| p720 | CTTTATTAAAATTGCCTTCAAGGGCAGCTT | 6744-6773 | ← | 8 |
| p722 | GATGAGGCCCTTTTGAAAGATTTCATTGAGGT | 6816-6847 | ← | 9 |
| p730 | CAAAATTTGAAACTATTGAAACATTATCTTTTATA | 6296-6331 | → | 10 |
| p731 | TATAAAAGATAATGTTTCAATAGTTTCAAATTTTGG | 6296-6331 | ← | 11 |
| p734 | ATGTTCAGGAGTATCATCAGTTGCATAACAAA | 6411-6442 | ← | 12 |
| p735 | CTCTTCTTCCCCATAATGCAGCTTCTTCTTGAATTG | 6462-6496 | ← | 13 |
| p738 | ACGAGCTGTGAACTCACCAAGAATCCAACGTT | 5715-5746 | ← | 14 |
| p739 | TAACATCCTACAGCACAATTTTCATCCCAAGCA | 5752-5784 | ← | 15 |
| p748 | GCAGTTGTAAGTTTCCAACCATTAGTAACCGTCAAT | 4648-4683 | ← | 16 |
| p750 | TTGAATATGCAATTGAATTGAACGTCAACAACTCTA | 4738-4773 | ← | 17 |
| p752 | AATCCATTTACATCGGGTAAAGTAAGAACTTCCTGCT | 3660-3696 | ← | 18 |
| p754 | ATACAATTTTCATCATTAGCAATCATATAAATCTGA | 3754-3789 | ← | 19 |
| p755 | GGTGAAAGATACATTTTCCAATCAAAATGCAAAAG | 2663-2697 | ← | 20 |
| p756 | CCAATTCAAAAGGATTATTGAAAGAAACTCTATGAA | 2589-2624 | ← | 21 |
| p762 | ATGTTCAATATCTGCAGCAGCACAATTAAAATATGC | 1502-1537 | ← | 22 |
| p763 | ATTTACAGTTGCAAATACCAATTCAAATGGACATGGA | 1546-1582 | ← | 23 |
| P764 | TGATAATTTCCTTGGTATTCCTAATTATAAATTTGCT | 1039-1075 | → | 24 |
| p767 | ATTTCACTTTGTTTATCTTTAGGACAATCACGA | 1135-1167 | ← | 25 |
| p769 | GCAAATGCTACTAATCTTAAAATTGGATCAGAGG | 2003-2036 | → | 26 |

TABLE 4-continued

Oligonucleotide primers used throughout the studies.

| Oligonucleotide Designation | Oligonucleotide (5'-3') | Genome Position | Orientation | SEQ ID NO |
|---|---|---|---|---|
| p770 | TGATGGTGATTATGTTTATATTTCTGAGCATAAAATTC | 2938-2975 | → | 27 |
| p771 | AGAAGAGCTTTATGATGCTGAAAATTGTAATACTGTTC | 4042-4079 | → | 28 |
| p772 | AGTTGAAAATGAAACAGTTGAAATTTTAGGTATAACTCA | 5038-5076 | → | 29 |
| p775 | CATAATATTACTGATGTTGTGGTTTCTTCAAAACC | 8038-8072 | →30 | 30 |
| p787 | CATGATTTTGTTGTTCAATAGGTTCATAAATATGTTCCTCAT | 9689-9730 | ← | 31 |
| p791 | TTTTAAAATAGGAAATTAAAGTCCAGTAAGGTTACTG | 1-37 | → | 33 |

EXAMPLE 4

SINV-3-uninfected laboratory-reared-newly mated queen monogyne colonies were identified by RT-PCR. These colonies were at an early stage of establishment, comprised of approximately 1 ml of brood and approximately 100 workers. Three colonies were infected by feeding them a purified preparation (see above) of SINV-3 in an approximately 10% sucrose solution. QPCR was conducted on the purified preparation to determine the concentration of viral particles. The preparation was diluted in approximately 10% sucrose to achieve a concentration of approximately $1 \times 10^6$ SINV-3 particles per µl/ml. This solution was placed into a small glass test tube with a cotton stopped end. The ant colonies were allowed to feed on the virus preparation for about three days and then the glass test tube was removed. Afterward, the ants were fed unadulterated approximately 10% sucrose, water, frozen crickets (Acheta domesticus), and egg yolk (hard-boiled) ad libitum. Worker ants (n=10) from each colony were examined for the presence of SINV-3 by extracting total RNA and conducting QPCR on 0, 7, 14, and 21 days after exposure to the SINV-3 preparation.

Mortality tests were conducted with a SINV-3 purified preparation. Worker ants (n=30) from a single SINV-3-negative field colony were individually dipped into an aqueous solution of SINV-3 particles (approximately $1 \times 10^{10}$ genome equivalents/µl). The ants were subsequently dried of excess water by placing them on a paper towel briefly. They were then held in small soufflé cups (30 ml) with water and approximately 10% sucrose. Mortality was monitored every two days. Control ants were dipped into water only.

QPCR was conducted to separately quantify the plus (genomic) and minus (replicative) RNA strands of SINV-3. cDNA was synthesized from the SINV-3 plus strand with oligonucleotide primer p707 (SEQ ID NO 4 ) and minus strand with oligonucleotide primer p705 (SEQ ID NO 2) as described above in example 3. After cDNA synthesis, the RNA templates were digested with RNase A and RNase H at approximately 37 degrees C. for about 30 minutes. QPCR was conducted as described in Example 3 with oligonucleotide primers p705 (SEQ ID NO 2 ) and p707 (SEQ ID NO 4).

SINV-3 was successfully transmitted to uninfected workers by feeding (FIG. 7). SINV-3 genome was detected within approximately 7 days of providing uninfected S. invicta ants a sucrose solution containing purified SINV-3. SINV-3 was detectable for at least 21 days after treatment indicating sustained infection among recipient colonies. Furthermore, minus (replicative) strand of SINV-3 was detected in worker ants indicating replication of the virus.

S. invicta worker ants that were dipped in a solution containing $10^{10}$ SINV-3 genome equivalents exhibited significantly higher cumulative mortality compared with worker ants dipped in water only (FIG. 8). No significant differences in mortality were observed between SINV-3 exposed and unexposed worker ants during the first 6 days of the experiment. However, significant mortality was observed on days 8 through 16. Interestingly, no significant mortality was detected among worker ants injected with purified preparations of SINV-3 compared with the control (data not shown).

The foregoing detailed description is for the purpose of illustration. Such detail is solely for that purpose and those skilled in the art can make variations without departing from the spirit and scope of the invention.

We claim:

1. A purified *Solenopsis invicta* virus having SEQ ID NO: 1.

2. A biocontrol composition comprising:
   a. an effective amount of *Solenopsis invicta* virus 3 having SEQ ID NO: 1 to at least reduce the number of fire ants in a colony, and
   b. a carrier.

3. The composition of claim 2 wherein said carrier is a food source for said ants.

4. The composition of claim 3 wherein said food source is selected from the group consisting of insects, cooked egg yolk, corn cob grits, soybean oil, extruded corn pellets, and mixtures thereof.

5. A biocontrol method comprising:
   a. spreading a composition of claim 2 at or near a fire ant colony.

6. The biocontrol method of claim 5 wherein said composition is the composition of claim 3.

7. The biocontrol method of claim 5 wherein said composition is the composition of claim 4.

* * * * *

SEQUENCE LISTING

<160> NUMBER OF SEQ ID NOS: 68

<210> SEQ ID NO 1
<211> LENGTH: 10411
<212> TYPE: DNA
<213> ORGANISM: Solenopsis invicta virus 3

<400> SEQUENCE: 1

```
ttttaaaata ggaaattaaa gtccagtaag gttactggca tttctatttt aactcaaagc      60
cttccgattc gggtttgcga gaatcaacgc catgtctgaa aagacacaaa ctttcgttca     120
aaatgaaact catgttttag acatgacttc tgattttaaa tcagacttat cacttgaaaa     180
```

```
agtgacttca tcagttgaac aaactgatga cttagttagt aaaatcatta ataataatga    240
cttagatatt aaggatcttt ccttttaag gaacttactt ttaagtactt tgcaatattt     300
aggtattgct aaatttgtag ctattaatat tactttaagt atcttaagta ttttaatgtt    360
acttataaac tcttgtgcta agtttactcg tattgttaat ttaagtagtc atattttaaa    420
tattataact actttaggct tatacttcca ggtatcctct atggagattg aagaaataac    480
ccaaactttt gaaatgaat tcggaactta tgatgatga aaaattttat ctcactatat     540
taaaatttgt aacttaccta atcgtaaaga tgtatatgaa tatatatctt taaatgattt    600
aaaatataaa ataaaacttc cggatatttc tttttatgaa cttaaaaatg atatactttc    660
aaaaaataaa aatttacact tatggatttt ccaaaaattt actgatgaat ttcttgctat    720
gtggtttggt gttcaacctt atcgtatttc aaatcttcgt gaaatgttag taatatctcg    780
tcaaggattt attcctaaag atttatttaa tgaaattcga aaattatgta atatgggtgt    840
ttctgttata atttctttca ttcaatctaa attatttgat gaaccttta aaaagagaga     900 ttgtacccaa gctttaaaag atgcttctgt tatctcttct ccatttgata ctctctggaa    960
tcttatttct aaacaagttt gtgataattc tgctgaagag cgatttactc aaactatatt    1020
ggattttaca tctgaatttg ataatttcct tggtattcca aattataaat ttgctaaaaa    1080
tcaaaaattg gtaaatacta tttctaaatc tcttgatgct tgtgctaaat ttattcgtga    1140
ttgtcctaaa gataaacaaa ctgaaatttt tcctcttcaa ggattacata ctgcaacagt    1200
taaacgtcgt aatgaaattt taactaatgt tatgccaaaa tttgctcgtc aggaaccatt    1260
tgttgttctt tttcaaggac ctggtggtat tggtaaaact catcttgttc aacaattggc    1320
tactaaatgt gtaaattctt tttatcaaga tcacgaagat gattatattg aaatttcacc    1380
tgatgataaa tattggcctc ctctttctgg acaacgtgtt gcatttttg atgaagctgg    1440 taatttgaat gatttaactg aggatcttct tttcagaaat attaaaagta tttgttcacc    1500
tgcatatttt aattgtgctg ctgctgatat agaacataaa atttcccat gtccatttga    1560 attagtgttt gcaactgtaa atactgattt agatactctt caatctaaaa tttcttcaac    1620
atttggtcaa gcatctgttt ttccaatttg gcgtcgttgc attgttgttg agtgttcatg    1680
gaatgaaaaa gaattgggac ctttaatta taaaaatcct tctggtcatc gttctgatta    1740
tagtcatatt actatgaatt atatgtcata tgatgataaa actcaaaaat ggctttaga    1800 aaaagaaatt aattttgata ctttgtttga tatgattcgt ttaagattta gaaagaaaca    1860
acaagaacat gatactaaaa tttctattct taataatgaa attcaacgtc aatctaattc    1920
taaacaacat ttttctgtat gtttatatgg tgaacctggt caaggtaaaa catataatct    1980
taataaatta ataacaactt tgcaaatgc aactaatctt aaaattggat cagaggaaaa    2040
accttctatt catattttg atgattatat taaagatgaa aatgatgaaa attgctctaa    2100
atttatggat atttataata ataaattacc taataattct gtaatatttt ctgcaactaa    2160
tgtttatcct aaaactcatt tctttccaac attttttctta actaatttaa tatatgcttt    2220
tattcaacct tttaaacaag ttggactta tcgcagattg ggatttgatg gttatactga     2280
tattcctaat tcttctgtta atgctccaat ttttgtacaa aatttaaat tttatgaacg     2340 taaacaacat atttgttatt ttcttttccct tgaattcctt aaaaatataa tttgttatat    2400
cttcttcttt ttatacttcc cgttaaaatt tataaagaaa attgatttaa ttgaaataaa    2460
ggatgtgaac aaatatgttt atgatagata tataaacttc ttatctcttt ctaaacaat    2520 tgaaattgtt gaatacccctc ctaatttgga aaatgttgaa tttgatttta gatttaatat    2580
```

```
gaataaattt catagagttt cttttaataa tccttttgaa ttggataaat atattcattt    2640
taataaaaat tcctatgaaa atcttttgca ttttgattgg aaaatgtatc tttcacctag    2700
agttaaacat cgtcttgctt tatcttatga aaaattcttt ataacaattt ctgaagttaa    2760
caaagaaata ataattgaag aattaaaacg atatgtttta cttttttaaac aatttaatat    2820 tgatcctaat atggagataa atcttggaga atatggatca ttttattata ttaacggaaa    2880
aattcattta atgacaatta atattgaaag taatgtttct gaaattcccg ttttttactga   2940 tggtgattat gtttatattt ctgaacataa aatccctgta attgatttat ttgataacat    3000
taatataaat tcaaaatata atttgagttt cgatcaatct atagctctaa attcgtttaa    3060
aactggtgat tcattttatt ctaatgctaa agttaggaag agtttatcca aatttgttct    3120
tcttaattat caaactaaat ttaaattata tttaaaagaa gctaaagata aagtaaagaa    3180
ttttattgaa actccaattg gtcatttact ctcaatatta ttaaccattt tgttatttg     3240 ttatgcatca tttaaaattt attctaaatt ttcaaacttt ttctctaaag atcaagctat    3300
tgaagatcaa agaaaggag aaaagaaaat taagaaaata actaattatg attctgatgg     3360
tgttcaacct caacgtaaag gtgaaaagaa aattaagaaa gtaactaatt atgattctga    3420
tggtgttcaa cctcaaagta atgttaaagt tgaagaagaa attaaattag tatttgatcc    3480
aactggtcaa aaattacttt ttggaaatga tttcactagt gaacttgaaa ctttagttga    3540
acttgaaaaa gatgatgaag aatttactaa atctaaaata gataataaat ctatggctgg    3600
acttcgtaga aagtaagac gtagacgtta tgctagatct aagaaggctc aaatcgaaaa     3660
acaggaagtt ctcactttac ctgatgtaaa tggatttgaa ggtggtaaac cttatttcca    3720
aattgctgaa gaaaaagctc gtaaaaattt atgtcaaatt tatatgattg ctaataatga    3780
aaattgtatt gcttctaaat tttctgatca tattgtatgt tatggattat tgttttttaa    3840
aaagagatta gcttcagttg gtcatattgt agaagcactt aagtgcgctc ctggttataa    3900
tctttatgct ggatgtgatc aatttaatgg taaattatat aaaatgaatc ttgttcgaaa    3960
ttatcgtaag agggaacttt ctgtttggga tgtcgattgt ccaaatgatt ttgtagattt    4020
aacttcgttt tcattcccta agaagagct ttatgatgct gaaaattgta atactgttct      4080
tggtcgtttt ggaatgaaca aacgagaagt atttatat ggtaactgcg aatttattca      4140
agaattcttt aaagtagata ataagggcgc tcaagaattt ggatatattg attgggctac    4200
agtagatata actttaacta caggtggaga ttgtggttta ccctattata tctgtgaaag    4260
gaagaaattc cataataaaa taatgggatt acattttgct ggtaataatg ttaatcataa    4320
aacaattggt atgtctgctt taatttataa ggaagatctt gtagtttgga aaggagctga    4380
acgtcaatct aaatgtaaat tttgtgatgt taaagatata attattgcac aacctgatat    4440
tccaaaggaa aaatataaag gttataatca tgaaattgtg tggaattcac ttcatgaatc    4500
ctcaccaaca accttaaatg aagaattgga acattattta aatattttcc ctaaatttac    4560
aggaacaata attaagcatt ctggtgataa attttatgga agcgtaaaac attctcatac    4620
tcaatttatt tctaaatta aaacagaatt gacagttact aatggttgga acttcaac      4680 tgctggtgat tgtcaatttg aatctaatca tattctcct aatactgaag taatgtatag     4740
agttgttgac gttcaattca attcgatatt taaagcattt aaatcacaac cttatattaa    4800
aaatttccgt ttaattgcaa atgtatatga aaagatgga aaacaacgtg taactatttt     4860
aacaataatt cccgtttctg attttaacgt aaaacaacaa actgttcgtc aagcattagt    4920
tccgctgcat cttaatgaag atgaggaagt ctatgttaca gaagatgttt ctgatatctt    4980
```

-continued

```
caaaacagct ataaaacgaa aacagcgtgg tatacttcct gatgtgccat acgaaacagt      5040
tgaaaatgaa acagttgaaa ttttaggtat aactcataga aatatgactc ctgaaccagc      5100
tcaaatgtat aaaccaactc cattctataa attagcatta aaatttaatt tagatcataa      5160
attacctgtt aattttaata tgaaagattg cccacaagaa caaaaagaca tgatggttct      5220
agatcgtttg ggacaaccaa accctagaat tactcaatct ttaaaatggg cacataaaga      5280
ttattcaccc gattacgaat taagaaaata tgttaaggaa caatatatgt gtaatataat      5340
ggaatattat gctggatgta acctttgac tgaagaacaa attttaaaag gttatggtcc       5400
taatcataga ttatatggag cacttggtgg aatggaaatt gattcatcta taggatggac      5460
aatgaaagaa ttatatcgag taactaaaaa gagtgatgtt ataaatttag attcaaacgg      5520
taattattct tttcttaaca atgaagctgc tcaatataca caagagcttt taaaaatttc      5580
tatggaacaa gcacataatg gtcaacgtta ttatactgct tttaatgaat taatgaaaat      5640
ggaaaaatta aaaccttcaa aaaatttat ccctagaact tttactgctc aagatttaaa       5700
tggagttctt atggaacgtt ggattcttgg tgagttcaca gctcgtgcac ttgcttggga      5760
tgaaaattgt gccgtaggat gtaatccata tgcaacattt cataaatttg ctacaaaatt      5820 cttttaatttt aaaaatttct tttcttgtga ttataaaaat tttgatagaa caattccaaa     5880
atgtgttttt gaagatttta gagatatgct tattcaagct aatcctcata tgaaaaatga     5940
aatttatgct tgtttccaaa caataattga tcgtatacaa gtaagtggaa attcgatatt      6000
acttgtacat ggtggtatgc cttcaggatg tgtaccaact gctccattga attctaaagt      6060
taatgatata atgattata cagcttatgt taatatatta agacgtgctg atagaggtga       6120
tataacttct tatcgttact atagagattt agtttgtaga ttatttatg gagatgatgt       6180 tattatagca gttgatgatt caattgctga catctttaat tgccaaacac tttctgaaga      6240
aatgaaaatc ttatttggta tgaatatgac tgatggttct aaaagcgata ttattccaaa      6300
atttgaaact attgaaacat tatctttttat atctagattt ttccgaccac ttaaacatca     6360
agaaaatttt tagttggtg ctttaaagaa aatttctatt caaactcatt tttattatgc       6420
aactgatgat actcctgaac atttcggtca agtatttaaa acaattcagg aagaagctgc      6480
attatgggaa gaagaatatt tcaataaaat tcaatcgtat attcaagaaa ttataagaaa      6540
atttccagaa atttctaaat tctttaattt tgaatcttat aaatcaattc aaaaacgata      6600
tattatgaat ggttggaatg aatttgtcaa acttgaaaag cttgacttaa atttaaataa      6660 gaaaagtcc agtaaggtta ctggcatcca ttcgaaacaa tattcgaagt ttcttaagtt       6720
tttgtcgaga atcgaaaacg aaaaagctgc ccttgaaggc aattttaata agaaagtgt       6780 taatacctgg tatttaaga tgtcaaaggc tatgcacctc aatgaaatct ttcaaaaggg       6840
cctcatctct aaaccccttg ctgaatttta ttttaacgag ggtcaaaaaa tgtgggattg      6900
caatattact ttccgtcgtt ctaaagacga tctccctttt acgttctctg gctcaggcac      6960
tacaaaagct tgtgcgcgtg aacaggccgc tgaagaagcg cttgttctct ttagccaaga     7020
agatgaaata gttcgtcaaa taacgatat tcaatcagat tgtaaattt gtaagaaaat        7080 gattcgatat aaaaaacttt tatctggtgt ttcaattcaa cgtcaaatga atgtttcaaa      7140
aattaccgaa atcatgttc cttctgctgg tatgatggca acagatcctt ctgttgctcc       7200
agattctggc attgcaacta atacacaaac tccttcgatt tcccgtgtat tgaatcccat      7260
agctagagca ttagataatc ctgctggaac tggtgctccc ttcgataaac atacttatgt      7320
ttataatgtc tttactcgtt ggccggaaat gagtaccgta gttaacaaat cattggctgc      7380
```

-continued

```
tggagctgaa gtatttaaaa tttctcttga tcctaataaa ttacctaaaa gaattttaca    7440
atatattcaa tttcataaaa ctataattcc tcaaatagaa gttcaaattc ttattggtgg    7500
tgctgctgga acagttggtt ggcttaaagt cggctgggtt cctgatgcaa gtactgctaa    7560
aaagtattca ttgatgatt tacaattggt tgcttcagaa acaattaatt tgaattcaac     7620
aataacaatg tcgatgataa taaatgatag ccgtagaaat ggtatgttta ggcttactaa    7680
aagtgatcct gaaccttggc ctggtattgt ttgtttagtc gaacatccta taactaatgt    7740
tcaaagaaat gatgatgtta attatccagt tattgttagt gttagacttg gtcctgattg    7800
ccagctaatg cagccttaca atgatttaaa ctgagtggag gcacagatcc agatcctgat    7860
cctgaaccgg atccggatcc agagcctggg cccgaccctg aaccaggggt cgatgaactc    7920
gatcttagta atatattcc aaatcaactt attgatttgc ttatttgtaa tagttatgtt     7980
ccaaataatg taagcgttga ttttctaagt acctatccaa atttaaattt ttcaattcat    8040
aatataactg atgttgtggt ttcttcaaaa ccatatacac ttgctctttt tgaaactgaa    8100
agtcaaatta attctgctag tgtttggaga ggtgatttaa ctcaattaag tgtttttatt    8160
caatataaat tttatactcg tgtagaagca tataataaag taactacagt tcatacagat    8220
aaatggactc caaatttcga tggtactgtt tataaacctg tggatgttaa aattgaacat    8280
gcatatggaa cttatgaatt aacaacaatg tggctaactt cttatggatt ggttatggaa    8340
tggtcactag atgaaagtag agtctttat ggtacttata aaactgattc taatggtcgg     8400
agatggttaa ttgatggtaa cacaccaatt gctagatctg atcattgttt catcgttca     8460
tcacctgatc ttcttagtga tgataaagct tactataata accctattgg agcaaaacaa    8520
ggtggaaagc ttgttgatgg agcacagatt taccgtatat ttaaaactga agtggagga    8580
tatcgctctg atccttttgt ccctgaaaca tattggccat ctgaaactcc ttataatgct    8640
gattggtcag gtgttaaaat gccttatcaa attagaaaag taattcaaac tggaaataat    8700
ttagcaggaa aacatcttga tggagatctt aaaatgtgtg ctatgataag gcaaggttcc    8760
tctagcactc aatctactga taattatttc tacccaattt atgttcataa tttctctgca    8820
ttgttaaaac aaatgaattt aatttttaaaa gaacgaaaaa ctaaatatat taaatttgat    8880
ttacaagtgg gtggcaaacc atttgctcaa atgggctttg gtgatggcgc ctttattgga    8940
agaactacaa tgtttagaca aattcgggct gctataacaa atgttatttt acttaaaaat    9000
atcgttggcg tagatgattt atctggatta caagcattac caacttctgg ttttgctgat    9060
tgggttgtta aagctcaatc tacaaattca aaatttttaa atgattttta taatgataaa    9120
atttcaatag aacgtcaagc gagtcttgga attgctgctg ctattggtgc tggtcaagga    9180
cttttcgggg gactttcagc ccaatggcaa tgcaacaac aagcagattg gtctcgtcaa     9240
atgcagagag aacgacttga tatgatggaa aaattagcaa atataaataa tcaagctcgt    9300
ttaaatcaat taacccaatc tggagctcaa caaagaataa ctcaacaagc tgcttatcaa    9360
caacaaatga atgctcttgg agctggttct gtgtccgctc aaaatggtat gtatactcca    9420
tctaattata caccattacc tagttataag tcaaatacta ctaattatta taataatagt    9480
gtttatcata ctgataataa tattactaat aatccttcta atacatcttt aactaataat    9540
attaataatt ttaatcctga attatttcaa caacaaagag aacgtatgcc tactccatca    9600
gaagcatatg ataattctaa aggttttgta cctcaacctg ggacatcaaa atctattgct    9660
actgaaaata ttaatccaaa ttataaagat gaggaacata tttatgaacc tattgaacaa    9720
caaaatcatg aatatgctga tattgattat aacgctatga atatttcgcg tgaaaataaa    9780
```

-continued

```
aactcttcta attttggaaa tgttggcatt ttggatcatc aatatgctga tattgattat    9840
gatgctatga aaatagctcg tgatcaacaa aattcaagta aatttggtaa tgttggtgtt    9900
ttaaaccatc aatatgctga attagatttt tcaaaaaata atacacgtaa aaattcacaa    9960
attttggata attctttata ttctaaaact caaccatctt caaaaatgat tgataattct   10020
ttatatggaa taaatccaaa taaaatggtt gaaaatcaaa attatgaacc tgcttctatg   10080
gaacgtaaaa attcaattta ttcttcaaat ttaaattctt ctaataattt gaaatttaat   10140
aatattccaa attttaaagg tcctactaat ttaaatattt ctggtgctaa acctgcagga   10200
tttggttctg gaataattca accagctatt aataaatata ctgactttc gaaacctaat    10260 taatcttaga ttttaaatcc acacttaatt ttaagttagt tatttaaatg tttgttttaa   10320
tttttgtttg atcttcgcat ttttgtggag gtgcgaagat taatcataat gtaaagtttt   10380
tcaaacaaaa aaaaaaaaa aaaaaaaaa a                                   10411
```

<210> SEQ ID NO 2
<211> LENGTH: 31
<212> TYPE: DNA
<213> ORGANISM: Solenopsis invicta virus 3

<400> SEQUENCE: 2
ctgctggtat gatggcaaca gatccttctg t        31

<210> SEQ ID NO 3
<211> LENGTH: 34
<212> TYPE: DNA
<213> ORGANISM: Solenopsis invicta virus 3

<400> SEQUENCE: 3
acagaaggat ctgttgccat catcatacca gcag        34

<210> SEQ ID NO 4
<211> LENGTH: 35
<212> TYPE: DNA
<213> ORGANISM: Solenopsis invicta virus 3

<400> SEQUENCE: 4
aaggagtttg tgtattagtt gcaatgccag aatct        35

<210> SEQ ID NO 5
<211> LENGTH: 31
<212> TYPE: DNA
<213> ORGANISM: Solenopsis invicta virus 3

<400> SEQUENCE: 5
atgctctagc tatgggattc aatacacggg a        31

<210> SEQ ID NO 6
<211> LENGTH: 36
<212> TYPE: DNA
<213> ORGANISM: Solenopsis invicta virus 3

<400> SEQUENCE: 6
catcatttct tgaacattag ttataggatg ttcgac        36

<210> SEQ ID NO 7

<400> SEQUENCE: 7

000

-continued

<210> SEQ ID NO 8
<211> LENGTH: 30
<212> TYPE: DNA
<213> ORGANISM: Solenopsis invicta virus 3

<400> SEQUENCE: 8
ctttattaaa attgccttca agggcagctt 30

<210> SEQ ID NO 9
<211> LENGTH: 32
<212> TYPE: DNA
<213> ORGANISM: Solenopsis invicta virus 3

<400> SEQUENCE: 9
gatgaggccc ttttgaaaga tttcattgag gt 32

<210> SEQ ID NO 10
<211> LENGTH: 35
<212> TYPE: DNA
<213> ORGANISM: Solenopsis invicta virus 3

<400> SEQUENCE: 10
caaaatttga aactattgaa acattatctt ttata 35

<210> SEQ ID NO 11
<211> LENGTH: 36
<212> TYPE: DNA
<213> ORGANISM: Solenopsis invicta virus 3

<400> SEQUENCE: 11
tataaaagat aatgtttcaa tagtttcaaa ttttgg 36

<210> SEQ ID NO 12
<211> LENGTH: 32
<212> TYPE: DNA
<213> ORGANISM: Solenopsis invicta virus 3

<400> SEQUENCE: 12
atgttcagga gtatcatcag ttgcataaca aa 32

<210> SEQ ID NO 13
<211> LENGTH: 36
<212> TYPE: DNA
<213> ORGANISM: Solenopsis invicta virus 3

<400> SEQUENCE: 13
ctcttcttcc ccataatgca gcttcttctt gaattg 36

<210> SEQ ID NO 14
<211> LENGTH: 32
<212> TYPE: DNA
<213> ORGANISM: Solenopsis invicta virus 3

<400> SEQUENCE: 14
acgagctgtg aactcaccaa gaatccaacg tt 32

<210> SEQ ID NO 15
<211> LENGTH: 33
<212> TYPE: DNA
<213> ORGANISM: Solenopsis invicta virus 3

<400> SEQUENCE: 15
taacatccta cagcacaatt ttcatcccaa gca 33

```
<210> SEQ ID NO 16
<211> LENGTH: 36
<212> TYPE: DNA
<213> ORGANISM: Solenopsis invicta virus 3

<400> SEQUENCE: 16
gcagttgtaa gtttccaacc attagtaacc gtcaat                              36

<210> SEQ ID NO 17
<211> LENGTH: 36
<212> TYPE: DNA
<213> ORGANISM: Solenopsis invicta virus 3

<400> SEQUENCE: 17
ttgaatatgc aattgaattg aacgtcaaca actcta                              36

<210> SEQ ID NO 18
<211> LENGTH: 37
<212> TYPE: DNA
<213> ORGANISM: Solenopsis invicta virus 3

<400> SEQUENCE: 18
aatccattta catcgggtaa agtaagaact tcctgct                             37

<210> SEQ ID NO 19
<211> LENGTH: 36
<212> TYPE: DNA
<213> ORGANISM: Solenopsis invicta virus 3

<400> SEQUENCE: 19 atacaattt catcattagc aatcatataa atctga                               36

<210> SEQ ID NO 20
<211> LENGTH: 35
<212> TYPE: DNA
<213> ORGANISM: Solenopsis invicta virus 3

<400> SEQUENCE: 20
ggtgaaagat catttttcca atcaaaatgc aaaag                               35

<210> SEQ ID NO 21
<211> LENGTH: 36
<212> TYPE: DNA
<213> ORGANISM: Solenopsis invicta virus 3

<400> SEQUENCE: 21
ccaattcaaa aggattattg aaagaaactc tatgaa                              36

<210> SEQ ID NO 22
<211> LENGTH: 36
<212> TYPE: DNA
<213> ORGANISM: Solenopsis invicta virus 3

<400> SEQUENCE: 22
atgttcaata tctgcagcag cacaattaaa atatgc                              36

<210> SEQ ID NO 23
<211> LENGTH: 37
<212> TYPE: DNA
<213> ORGANISM: Solenopsis invicta virus 3

<400> SEQUENCE: 23
atttacagtt gcaaatacca attcaaatgg acatgga                             37
```

```
<210> SEQ ID NO 24
<211> LENGTH: 37
<212> TYPE: DNA
<213> ORGANISM: Solenopsis invicta virus 3

<400> SEQUENCE: 24
tgataatttc cttggtattc ctaattataa atttgct                              37

<210> SEQ ID NO 25
<211> LENGTH: 33
<212> TYPE: DNA
<213> ORGANISM: Solenopsis invicta virus 3

<400> SEQUENCE: 25
atttcacttt gtttatcttt aggacaatca cga                                  33

<210> SEQ ID NO 26
<211> LENGTH: 34
<212> TYPE: DNA
<213> ORGANISM: Solenopsis invicta virus 3

<400> SEQUENCE: 26
gcaaatgcta ctaatcttaa aattggatca gagg                                 34

<210> SEQ ID NO 27
<211> LENGTH: 38
<212> TYPE: DNA
<213> ORGANISM: Solenopsis invicta virus 3

<400> SEQUENCE: 27
tgatggtgat tatgtttata tttctgagca taaaattc                             38

<210> SEQ ID NO 28
<211> LENGTH: 38
<212> TYPE: DNA
<213> ORGANISM: Solenopsis invicta virus 3

<400> SEQUENCE: 28
agaagagctt tatgatgctg aaaattgtaa tactgttc                             38

<210> SEQ ID NO 29
<211> LENGTH: 39
<212> TYPE: DNA
<213> ORGANISM: Solenopsis invicta virus 3

<400> SEQUENCE: 29
agttgaaaat gaaacagttg aaattttagg tataactca                            39

<210> SEQ ID NO 30
<211> LENGTH: 35
<212> TYPE: DNA
<213> ORGANISM: Solenopsis invicta virus 3

<400> SEQUENCE: 30
cataatatta ctgatgttgt ggtttcttca aaacc                                35

<210> SEQ ID NO 31
<211> LENGTH: 42
<212> TYPE: DNA
<213> ORGANISM: Solenopsis invicta virus 3

<400> SEQUENCE: 31
catgattttg ttgttcaata ggttcataaa tatgttcctc at                        42
```

-continued

```
<210> SEQ ID NO 32
<400> SEQUENCE: 32

000

<210> SEQ ID NO 33
<211> LENGTH: 37
<212> TYPE: DNA
<213> ORGANISM: Solenopsis invicta virus 3

<400> SEQUENCE: 33
ttttaaaata ggaaattaaa gtccagtaag gttactg                                37

<210> SEQ ID NO 34
<211> LENGTH: 70
<212> TYPE: PRT
<213> ORGANISM: Solenopsis invicta virus 3

<400> SEQUENCE: 34
```

Leu Lys Asp Glu Lys Leu Lys Ile Gln Lys Thr Tyr Lys Gly Arg Gln
1               5                   10                  15

Phe Ser Ala Ala Asp Phe Leu Leu Ile Leu Leu Glu Arg Lys Tyr Leu
            20                  25                  30

Gly Gln Phe Leu Ala Lys Ala Val Lys Tyr Asp Lys Glu Val Ala Val
        35                  40                  45

Gly Met Asp Pro Ile Leu Asp Phe His Glu Val Asp Phe Val Ser Trp
    50                  55                  60

Asp Lys Lys Ile Pro Ala
65                  70

```
<210> SEQ ID NO 35
<211> LENGTH: 70
<212> TYPE: PRT
<213> ORGANISM: Solenopsis invicta virus 3

<400> SEQUENCE: 35
```

Met Lys Met Glu Lys Leu Lys Pro Ser Lys Asn Phe Ile Pro Arg Thr
1               5                   10                  15

Phe Thr Ala Gln Asp Leu Asn Gly Val Leu Met Glu Arg Trp Ile Leu
            20                  25                  30

Gly Glu Phe Thr Ala Arg Ala Leu Ala Trp Asp Glu Asn Cys Ala Val
        35                  40                  45

Gly Cys Asn Pro Tyr Ala Thr Phe His Lys Cys Asp Tyr Lys Asn Phe
    50                  55                  60

Asp Arg Thr Ile Pro Lys
65                  70

```
<210> SEQ ID NO 36
<211> LENGTH: 75
<212> TYPE: PRT
<213> ORGANISM: Solenopsis invicta virus 3

<400> SEQUENCE: 36
```

Arg Pro Ile Asn Lys Val Leu Gly Asp Glu Thr Thr Pro Pro Lys Thr
1               5                   10                  15

Arg Ser Val Thr Cys Met Asn Val Tyr Tyr Ile Leu Ala Trp Arg Arg
            20                  25                  30

Tyr Thr Met Arg Phe Trp Ser Ala Met His Arg Ala Ala Asp Gly Thr
        35                  40                  45

Ser Met Phe Gly Pro Gly Ile Asn Pro Glu Gly Pro Glu Trp Ser Phe

```
                          50                  55                  60

Asp Val Ser Asn Trp Asp Gly Phe Leu Phe Ala
 65                  70                  75

<210> SEQ ID NO 37
<211> LENGTH: 74
<212> TYPE: PRT
<213> ORGANISM: Solenopsis invicta virus 3

<400> SEQUENCE: 37

Leu Lys Asp Glu Arg Arg Pro Ile Glu Lys Val Asp Ala Leu Lys Thr
 1               5                  10                  15

Arg Val Phe Ser Asn Gly Pro Met Asp Phe Asn Leu Ala Phe Arg Lys
             20                  25                  30

Tyr Phe Leu Gly Phe Ile Ala His Leu Met Glu Asn Arg Ile Asp Asn
         35                  40                  45

Glu Val Ala Ile Gly Thr Asn Val Tyr Ser Arg Asp Trp Thr Gly Asp
     50                  55                  60

Phe Ser Asn Phe Asp Gly Ser Leu Asn Ala
 65                  70

<210> SEQ ID NO 38
<211> LENGTH: 75
<212> TYPE: PRT
<213> ORGANISM: Solenopsis invicta virus 3

<400> SEQUENCE: 38

Pro Lys Asp Glu Leu Arg Pro Leu Glu Lys Val Leu Glu Ser Lys Thr
 1               5                  10                  15

Arg Ala Ile Asp Ala Cys Pro Leu Asp Tyr Ser Ile Leu Cys Arg Met
             20                  25                  30

Tyr Trp Gly Pro Ala Ile Ser Tyr Phe His Leu Asn Pro Gly Phe His
         35                  40                  45

Thr Gly Val Ala Ile Gly Ile Asp Pro Asp Arg Gln Trp Asp Glu Leu
     50                  55                  60

Asp Phe Ser Ala Phe Asp Ala Ser Leu Ser Pro
 65                  70                  75

<210> SEQ ID NO 39
<211> LENGTH: 63
<212> TYPE: PRT
<213> ORGANISM: Solenopsis invicta virus 3

<400> SEQUENCE: 39

Asn Gly Thr Met Ala Ser Gly Cys Val Ala Thr Ala Pro Leu Asn Ser
 1               5                  10                  15

Val Leu Asn Asn Phe Leu Met Gln Ile Ser Tyr Gly Asp Asp Lys Trp
             20                  25                  30

Ile Ser Thr Asp Leu Asp Trp Phe Asn Met Val Thr Pro Leu Asp Gln
         35                  40                  45

Ile Ser Leu Ile Ser Arg Tyr Pro Arg Lys Leu Pro Ser Gly Val
     50                  55                  60

<210> SEQ ID NO 40
<211> LENGTH: 68
<212> TYPE: PRT
<213> ORGANISM: Solenopsis invicta virus 3

<400> SEQUENCE: 40

His Gly Gly Met Pro Ser Gly Cys Val Pro Thr Ala Pro Leu Asn Ser
```

```
                1               5                   10                  15
Lys Val Asn Asp Ile Met Ile Arg Leu Phe Tyr Gly Asp Asp Val Ile
                20                  25                  30

Ile Ala Val Asp Asp Ser Ile Ala Asp Ile Phe Asn Cys Gln Thr Thr
                35                  40                  45

Ile Glu Thr Leu Ser Phe Ile Ser Arg Phe Arg Pro Leu Lys His
                50                  55                  60

Gln Glu Asn Phe
65

<210> SEQ ID NO 41
<211> LENGTH: 66
<212> TYPE: PRT
<213> ORGANISM: Solenopsis invicta virus 3

<400> SEQUENCE: 41

Ser Arg Gly Ile Ile Ser Gly Phe Pro Gly Thr Ala Glu Val Asn Thr
1               5                   10                  15

Leu Ala His Ile Leu Leu Ile Ala Ile Leu Tyr Gly Asp Asp Ile Leu
                20                  25                  30

Leu Thr Ile His Asp Asp Ile Leu His Leu Phe Asn Gly Lys Thr Pro
                35                  40                  45

Leu Ser Gln Cys Gln Phe Leu Lys Ser Ser Trp Arg Gln Leu Leu Pro
                50                  55                  60

Gly Tyr
65

<210> SEQ ID NO 42
<211> LENGTH: 67
<212> TYPE: PRT
<213> ORGANISM: Solenopsis invicta virus 3

<400> SEQUENCE: 42

Thr His Ser Gln Pro Ser Gly Asn Pro Ala Thr Thr Pro Leu Asn Cys
1               5                   10                  15

Leu Ile Asn Ser Ile Gly Leu Leu Ile Ser Tyr Gly Asp Asp Asn Val
                20                  25                  30

Ile Asn Ile His Pro Leu Ile Ser His Leu Phe Asn Met Asn Thr Thr
                35                  40                  45

Leu Glu Glu Val Ser Phe Leu Lys Arg Gly Phe Ile Phe Asn Glu Glu
                50                  55                  60

Arg Asn Cys
65

<210> SEQ ID NO 43
<211> LENGTH: 62
<212> TYPE: PRT
<213> ORGANISM: Solenopsis invicta virus 3

<400> SEQUENCE: 43

Cys Gly Ser Met Pro Ser Gly Ser Pro Cys Thr Ala Leu Leu Asn Ser
1               5                   10                  15

Ile Ile Asn Asn Val Asn Leu Cys Tyr Gly Asp Asp Val Leu Ile Val
                20                  25                  30

Phe Ser Arg Asp Val Gln Ile Asp Asn Leu Asp Leu Pro Val Ser Glu
                35                  40                  45

Leu Thr Phe Leu Lys Arg Ser Phe Asn Leu Val Glu Asp Arg
                50                  55                  60
```

```
<210> SEQ ID NO 44
<211> LENGTH: 58
<212> TYPE: PRT
<213> ORGANISM: Chaetocoelopa sydneyensis virus

<400> SEQUENCE: 44

Leu Lys Asp Glu Lys Leu Lys Ile Gln Lys Thr Tyr Lys Gly Arg Gln
1               5                   10                  15

Phe Ser Ala Ala Asp Phe Leu Leu Ile Leu Leu Glu Arg Lys Tyr Leu
            20                  25                  30

Gly Gln Phe Leu Ala Lys Ala Val Lys Tyr Asp Lys Glu Val Ala Val
        35                  40                  45

Gly Met Asp Pro Ile Leu Asp Phe His Glu
    50                  55

<210> SEQ ID NO 45
<211> LENGTH: 12
<212> TYPE: PRT
<213> ORGANISM: Chaetocoelopa sydneyensis virus

<400> SEQUENCE: 45

Val Asp Phe Val Ser Trp Asp Lys Lys Ile Pro Ala
1               5                   10

<210> SEQ ID NO 46
<211> LENGTH: 23
<212> TYPE: PRT
<213> ORGANISM: Chaetocoelopa sydneyensis virus

<400> SEQUENCE: 46

Asn Gly Thr Met Ala Ser Gly Cys Val Ala Thr Ala Pro Leu Asn Ser
1               5                   10                  15

Val Leu Asn Asn Phe Leu Met
            20

<210> SEQ ID NO 47
<211> LENGTH: 21
<212> TYPE: PRT
<213> ORGANISM: Chaetocoelopa sydneyensis virus

<400> SEQUENCE: 47

Gln Ile Ser Tyr Gly Asp Asp Lys Trp Ile Ser Thr Asp Leu Asp Trp
1               5                   10                  15

Phe Asn Met Val Thr
            20

<210> SEQ ID NO 48
<211> LENGTH: 19
<212> TYPE: PRT
<213> ORGANISM: Chaetocoelopa sydneyensis virus

<400> SEQUENCE: 48

Pro Leu Asp Gln Ile Ser Leu Ile Ser Arg Tyr Pro Arg Lys Leu Pro
1               5                   10                  15

Ser Gly Val

<210> SEQ ID NO 49
<211> LENGTH: 58
<212> TYPE: PRT
<213> ORGANISM: Solenopsis invicta virus 3

<400> SEQUENCE: 49
```

```
Met Lys Met Glu Lys Leu Lys Pro Ser Lys Asn Phe Ile Pro Arg Thr
1               5                   10                  15

Phe Thr Ala Gln Asp Leu Asn Gly Val Leu Met Glu Arg Trp Ile Leu
            20                  25                  30

Gly Glu Phe Thr Ala Arg Ala Leu Ala Trp Asp Glu Asn Cys Ala Val
        35                  40                  45

Gly Cys Asn Pro Tyr Ala Thr Phe His Lys
    50                  55

<210> SEQ ID NO 50
<211> LENGTH: 12
<212> TYPE: PRT
<213> ORGANISM: Solenopsis invicta virus 3

<400> SEQUENCE: 50

Cys Asp Tyr Lys Asn Phe Asp Arg Thr Ile Pro Lys
1               5                   10

<210> SEQ ID NO 51
<211> LENGTH: 23
<212> TYPE: PRT
<213> ORGANISM: Solenopsis invicta virus 3

<400> SEQUENCE: 51

His Gly Gly Met Pro Ser Gly Cys Val Pro Thr Ala Pro Leu Asn Ser
1               5                   10                  15

Lys Val Asn Asp Ile Met Ile
            20

<210> SEQ ID NO 52
<211> LENGTH: 24
<212> TYPE: PRT
<213> ORGANISM: Solenopsis invicta virus 3

<400> SEQUENCE: 52

Arg Leu Phe Tyr Gly Asp Asp Val Ile Ile Ala Val Asp Asp Ser Ile
1               5                   10                  15

Ala Asp Ile Phe Asn Cys Gln Thr
            20

<210> SEQ ID NO 53
<211> LENGTH: 21
<212> TYPE: PRT
<213> ORGANISM: Solenopsis invicta virus 3

<400> SEQUENCE: 53

Thr Ile Glu Thr Leu Ser Phe Ile Ser Arg Phe Phe Arg Pro Leu Lys
1               5                   10                  15

His Gln Glu Asn Phe
            20

<210> SEQ ID NO 54
<211> LENGTH: 63
<212> TYPE: PRT
<213> ORGANISM: Solenopsis invicta virus 2

<400> SEQUENCE: 54

Arg Pro Ile Asn Lys Val Leu Gly Asp Glu Thr Thr Pro Pro Lys Thr
1               5                   10                  15

Arg Ser Val Thr Cys Met Asn Val Tyr Tyr Ile Leu Ala Trp Arg Arg
            20                  25                  30

Tyr Thr Met Arg Phe Trp Ser Ala Met His Arg Ala Ala Asp Gly Thr
```

```
            35                  40                  45
Ser Met Phe Gly Pro Gly Ile Asn Pro Glu Gly Pro Glu Trp Ser
    50                  55                  60

<210> SEQ ID NO 55
<211> LENGTH: 12
<212> TYPE: PRT
<213> ORGANISM: Solenopsis invicta virus 2

<400> SEQUENCE: 55

Phe Asp Val Ser Asn Trp Asp Gly Phe Leu Phe Ala
1               5                  10

<210> SEQ ID NO 56
<211> LENGTH: 23
<212> TYPE: PRT
<213> ORGANISM: Solenopsis invicta virus 2

<400> SEQUENCE: 56

Ser Arg Gly Ile Ile Ser Gly Phe Pro Gly Thr Ala Glu Val Asn Thr
1               5                  10                  15

Leu Ala His Ile Leu Leu Ile
            20

<210> SEQ ID NO 57
<211> LENGTH: 24
<212> TYPE: PRT
<213> ORGANISM: Solenopsis invicta virus 2

<400> SEQUENCE: 57

Ala Ile Leu Tyr Gly Asp Asp Ile Leu Leu Thr Ile His Asp Asp Ile
1               5                  10                  15

Leu His Leu Phe Asn Gly Lys Thr
            20

<210> SEQ ID NO 58
<211> LENGTH: 19
<212> TYPE: PRT
<213> ORGANISM: Solenopsis invicta virus 2

<400> SEQUENCE: 58

Pro Leu Ser Gln Cys Gln Phe Leu Lys Ser Ser Trp Arg Gln Leu Leu
1               5                  10                  15

Pro Gly Tyr

<210> SEQ ID NO 59
<211> LENGTH: 62
<212> TYPE: PRT
<213> ORGANISM: Solenopsis invicta virus 1

<400> SEQUENCE: 59

Leu Lys Asp Glu Arg Arg Pro Ile Glu Lys Val Asp Ala Leu Lys Thr
1               5                  10                  15

Arg Val Phe Ser Asn Gly Pro Met Asp Phe Asn Leu Ala Phe Arg Lys
            20                  25                  30

Tyr Phe Leu Gly Phe Ile Ala His Leu Met Glu Asn Arg Ile Asp Asn
        35                  40                  45

Glu Val Ala Ile Gly Thr Asn Val Tyr Ser Arg Asp Trp Thr
    50                  55                  60

<210> SEQ ID NO 60
<211> LENGTH: 12
```

```
<212> TYPE: PRT
<213> ORGANISM: Solenopsis invicta virus 1

<400> SEQUENCE: 60

Gly Asp Phe Ser Asn Phe Asp Gly Ser Leu Asn Ala
1               5                   10

<210> SEQ ID NO 61
<211> LENGTH: 23
<212> TYPE: PRT
<213> ORGANISM: Solenopsis invicta virus 1

<400> SEQUENCE: 61

Thr His Ser Gln Pro Ser Gly Asn Pro Ala Thr Thr Pro Leu Asn Cys
1               5                   10                  15

Leu Ile Asn Ser Ile Gly Leu
            20

<210> SEQ ID NO 62
<211> LENGTH: 24
<212> TYPE: PRT
<213> ORGANISM: Solenopsis invicta virus 1

<400> SEQUENCE: 62

Leu Ile Ser Tyr Gly Asp Asp Asn Val Ile Asn Ile His Pro Leu Ile
1               5                   10                  15

Ser His Leu Phe Asn Met Asn Thr
            20

<210> SEQ ID NO 63
<211> LENGTH: 20
<212> TYPE: PRT
<213> ORGANISM: Solenopsis invicta virus 1

<400> SEQUENCE: 63

Thr Leu Glu Glu Val Ser Phe Leu Lys Arg Gly Phe Ile Phe Asn Glu
1               5                   10                  15

Glu Arg Asn Cys
            20

<210> SEQ ID NO 64
<211> LENGTH: 63
<212> TYPE: PRT
<213> ORGANISM: Hepatitis A virus

<400> SEQUENCE: 64

Pro Lys Asp Glu Leu Arg Pro Leu Glu Lys Val Leu Glu Ser Lys Thr
1               5                   10                  15

Arg Ala Ile Asp Ala Cys Pro Leu Asp Tyr Ser Ile Leu Cys Arg Met
            20                  25                  30

Tyr Trp Gly Pro Ala Ile Ser Tyr Phe His Leu Asn Pro Gly Phe His
        35                  40                  45

Thr Gly Val Ala Ile Gly Ile Asp Pro Asp Arg Gln Trp Asp Glu
    50                  55                  60

<210> SEQ ID NO 65
<211> LENGTH: 12
<212> TYPE: PRT
<213> ORGANISM: Hepatitis A virus

<400> SEQUENCE: 65

Leu Asp Phe Ser Ala Phe Asp Ala Ser Leu Ser Pro
1               5                   10
```

```
<210> SEQ ID NO 66
<211> LENGTH: 23
<212> TYPE: PRT
<213> ORGANISM: Hepatitis A virus

<400> SEQUENCE: 66

Cys Gly Ser Met Pro Ser Gly Ser Pro Cys Thr Ala Leu Leu Asn Ser
1               5                   10                  15

Ile Ile Asn Asn Val Asn Leu
            20

<210> SEQ ID NO 67
<211> LENGTH: 21
<212> TYPE: PRT
<213> ORGANISM: Hepatitis A virus

<400> SEQUENCE: 67

Cys Tyr Gly Asp Asp Val Leu Ile Val Phe Ser Arg Asp Val Gln Ile
1               5                   10                  15

Asp Asn Leu Asp Leu
            20

<210> SEQ ID NO 68
<211> LENGTH: 18
<212> TYPE: PRT
<213> ORGANISM: Hepatitis A virus

<400> SEQUENCE: 68

Pro Val Ser Glu Leu Thr Phe Leu Lys Arg Ser Phe Asn Leu Val Glu
1               5                   10                  15

Asp Arg
```